US012369869B2

(12) United States Patent
Behlmer et al.

(10) Patent No.: US 12,369,869 B2
(45) Date of Patent: Jul. 29, 2025

(54) SYSTEMS AND METHODS FOR AN INTEGRATED FILTER ASSEMBLY WITH TWO CARRIAGES

(71) Applicant: GE Precision Healthcare LLC, Wauwatosa, WI (US)

(72) Inventors: Timothy Behlmer, Milwaukee, WI (US); Brandon Smith, Waukesha, WI (US); Changlyong Kim, Brookfield, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 252 days.

(21) Appl. No.: 17/828,928

(22) Filed: May 31, 2022

(65) Prior Publication Data
US 2023/0380782 A1   Nov. 30, 2023

(51) Int. Cl.
*A61B 6/40*   (2024.01)
*A61B 6/00*   (2024.01)
*A61B 6/06*   (2006.01)
*A61B 6/58*   (2024.01)

(52) U.S. Cl.
CPC .............. *A61B 6/4042* (2013.01); *A61B 6/06* (2013.01); *A61B 6/4435* (2013.01); *A61B 6/488* (2013.01); *A61B 6/582* (2013.01)

(58) Field of Classification Search
None
See application file for complete search history.

(56) References Cited

U.S. PATENT DOCUMENTS

| 8,238,522 | B2* | 8/2012 | Frey .......................... A61B 6/06 378/158 |
| 8,853,636 | B2* | 10/2014 | Perkins ................ A61N 5/1042 378/65 |
| 11,147,528 | B2 | 10/2021 | Thibault |
| 11,160,518 | B2* | 11/2021 | Smith .................... A61B 6/488 |
| 11,229,412 | B2 | 1/2022 | Kawata |
| 11,673,004 | B2* | 6/2023 | Filiberti ................. H01H 13/70 378/148 |
| 11,712,216 | B2* | 8/2023 | Thibault .............. A61B 6/4488 378/109 |

(Continued)

FOREIGN PATENT DOCUMENTS

| EP | 3777687 A1 | 2/2021 |
| EP | 2634775 B1 | 9/2021 |
| WO | 2009096361 A1 | 8/2009 |

OTHER PUBLICATIONS

EP application 23175025.8 filed May 24, 2023—extended Search Report issued Nov. 6, 2023; 21 pages.

*Primary Examiner* — David P Porta
*Assistant Examiner* — Djura Malevic

(57) ABSTRACT

Various systems and methods are provided for an integrated filter assembly including at least one bowtie filter and at least one beam hardening filter mounted on a carriage. In one embodiment, an imaging system may include a first carriage including at least one beam hardening filter and at least one bowtie filter, a second carriage including at least two additional bowtie filters, and a carriage driving system for moving the carriages to selectively position the at least one beam hardening filter and one of the bowtie filters in a path of an X-ray beam. The at least one beam hardening filter may overlap with at least one of the bowtie filters.

21 Claims, 15 Drawing Sheets

(56) References Cited

U.S. PATENT DOCUMENTS

| | | | | |
|---|---|---|---|---|
| 2007/0025520 A1* | 2/2007 | Thandiackal | ............ | G21K 1/10 |
| | | | | 378/157 |
| 2013/0221243 A1* | 8/2013 | Perkins | .................... | G21K 1/04 |
| | | | | 378/65 |
| 2021/0045702 A1* | 2/2021 | Smith | .................... | A61B 6/488 |
| 2023/0380782 A1* | 11/2023 | Behlmer | .................. | A61B 6/06 |

* cited by examiner

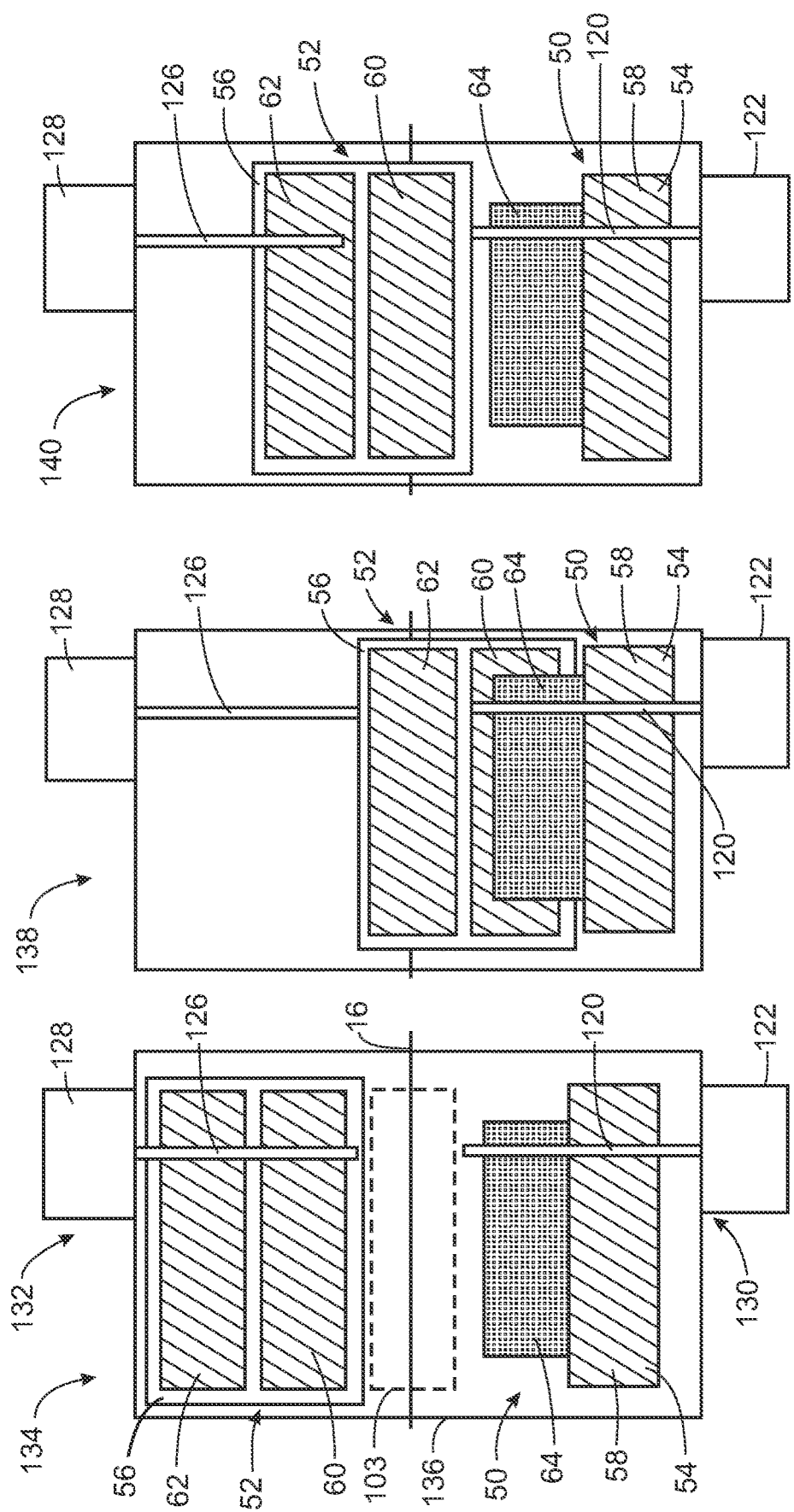

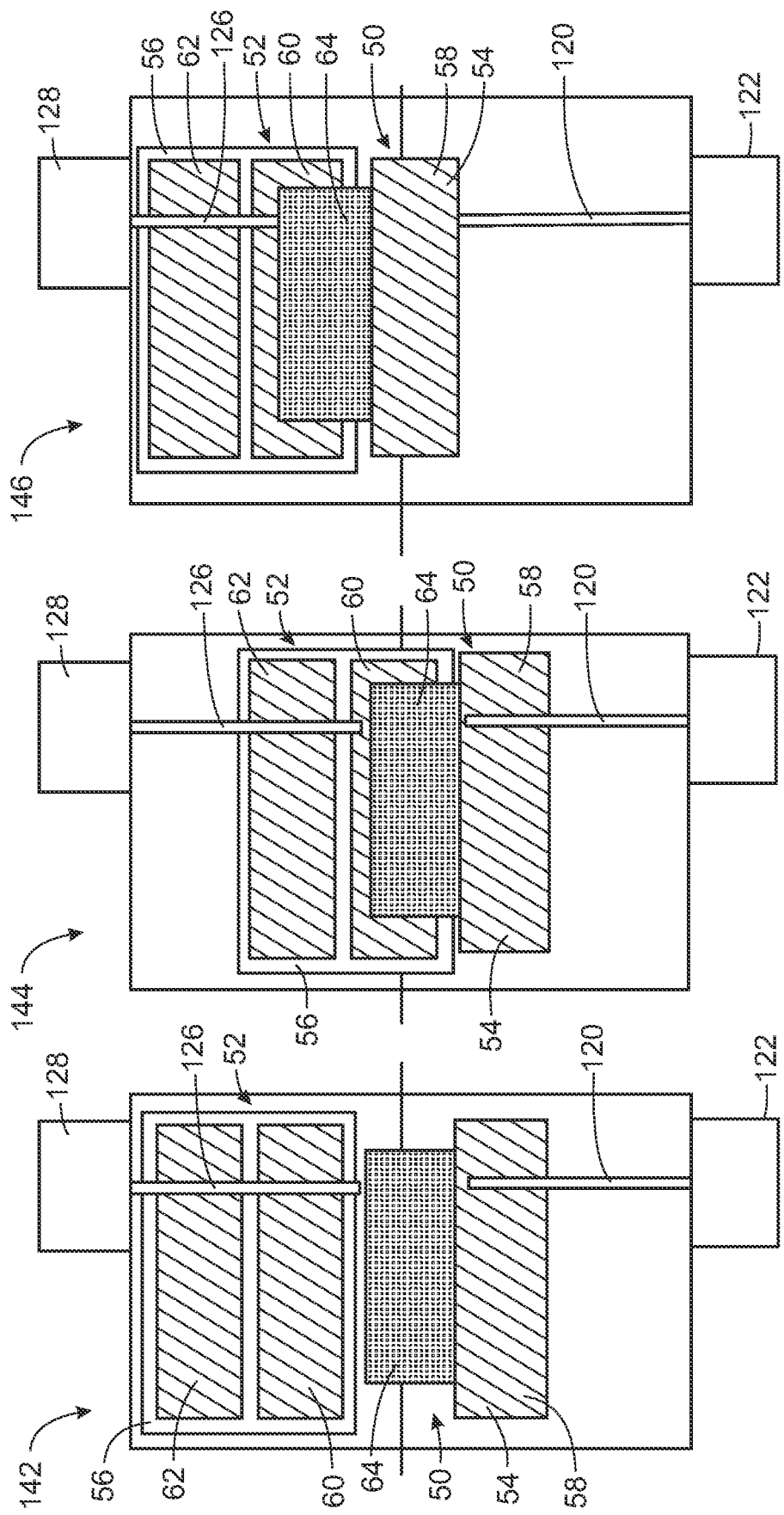

SYSTEMS AND METHODS FOR AN INTEGRATED FILTER ASSEMBLY WITH TWO CARRIAGES

FIELD

Embodiments of the subject matter disclosed herein relate to diagnostic imaging systems and methods, and more particularly, to a computed tomography (CT) imaging system with an integrated filter assembly.

BACKGROUND

Noninvasive imaging modalities may transmit energy in the form of X-ray radiation into an imaging subject. Based on the transmitted energy, images may be subsequently generated indicative of the structural or functional information internal to the imaging subject. In a computed tomography (CT) imaging system, an X-ray source generates and transmits X-rays toward an X-ray detector through the imaging subject, such as a patient. A bowtie filter may be positioned between the X-ray source and the imaging subject for adjusting the spatial distribution of the X-ray energy based on the anatomy of the imaging subject. The bowtie filter may be designed to distribute higher X-ray energy to specific imaging region of the subject. As a result, the quality amplitude of signal received by the X-ray detector is improved in the central area, and the X-ray dose on the periphery of the specific subject is reduced. Different anatomy of the subject may require different bowtie filters. For example, bowtie filters of different materials, shapes and sizes may be designed to image distinct regions of the subject's body such as the head, the chest, and the abdomen.

Further, a beam hardening filter may be positioned between the X-ray source and the imaging subject for absorbing or intercepting the lower energy X-rays, thereby attenuating, and "hardening" the X-ray beam. Conditioning of the X-ray beam via the beam hardening filter may be specifically desired during calibration or during a diagnostic patient scan or a scout scan which may precede a diagnostic scan and may provide a projection view along a longitudinal axis of the subject including the internal structure of the subject. Therefore, a system and method for integrating at least one beam hardening filter and one or more bowtie filters is needed.

BRIEF DESCRIPTION

In an aspect, a system comprising at least one carriage including at least one beam hardening filter and one or more bowtie filters, and a carriage driving system for moving the at least one carriage to selectively position the at least one beam hardening filter and the one or more bowtie filters in and out of a path of an X-ray beam between an X-ray source and a subject, the at least one beam hardening filter may be positioned in and out of the X-ray beam or may be used in combination with at least one of the one or more bowtie filters to be positioned in and out of the X-ray beam.

In an aspect, an imaging system, comprising a collimator assembly, the collimator assembly positioned adjacent to an X-ray source, the X-ray source generating an X-ray beam through the collimator assembly, wherein the collimator assembly includes at least one carriage including at least one beam hardening filter and at least one bowtie filter, wherein the beam hardening filter is coupled to an edge of the carriage and extend away from the at least one bowtie filter.

In an aspect, A method for an imaging system, comprising during a first imaging, moving a first carriage to position a beam hardening filter coupled to the first carriage in a path of an X-ray beam and moving a second carriage to position a second bowtie filter housed in the second carriage in the path of the X-ray beam; and during a second imaging, moving the first carriage to move the beam hardening filter out of the path of the X-ray beam.

In an aspect, A computed tomography (CT) imaging system, comprising a gantry; an X-ray source positioned in the gantry for emitting X-rays; an X-ray detector positioned in the gantry opposite the X-ray source; a first carriage including a first bowtie filter and a first beam hardening filter; a second carriage including a second bowtie filter and a third bowtie filter with a second beam hardening filter positioned between the second bowtie filter and the third bowtie filter; and a carriage driving system for switching filters by moving one or more of the first bowtie filter, the second bowtie filter, the third bowtie filter, and the first beam hardening filter, the second beam hardening filter into or out of an X-ray beam.

In an aspect, A pre-patient collimator assembly for a CT imaging system, the pre-patient collimator assembly comprising a first carriage including a beam hardening filter and a first bowtie filter; a first carriage driving system coupled to the first carriage for moving the first carriage and thus the beam hardening filter and the first bowtie filter in and out of an X-ray beam path; a second carriage including a second bowtie filter and a third bowtie filter; and a second carriage driving system coupled to the second carriage for moving the second carriage and thus the second bowtie filter and the third bowtie filter in and out of the X-ray beam path, wherein the beam hardening filter is positioned along and coupled to an outer edge of the first carriage, and wherein the beam hardening filter may be positioned in the X-ray beam path alone or in combination with one of the second bowtie filter or the third bowtie filter.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The subject matter of the disclosure will be better understood from reading the following description of non-limiting embodiments, with reference to the attached drawings, wherein below:

FIG. 11A shows a first position of a filter assembly with three bowtie filters and a beam hardening filter.

FIG. 11B shows a second position of the filter assembly of FIG. 11A.

FIG. 11C shows a third position of the filter assembly of FIG. 11A.

FIG. 11D shows a fourth position of the filter assembly of FIG. 11A.

FIG. 11E shows a fifth position of the filter assembly of FIG. 11A.

FIG. 11F shows a sixth position of the filter assembly of FIG. 11A.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Figure 1:
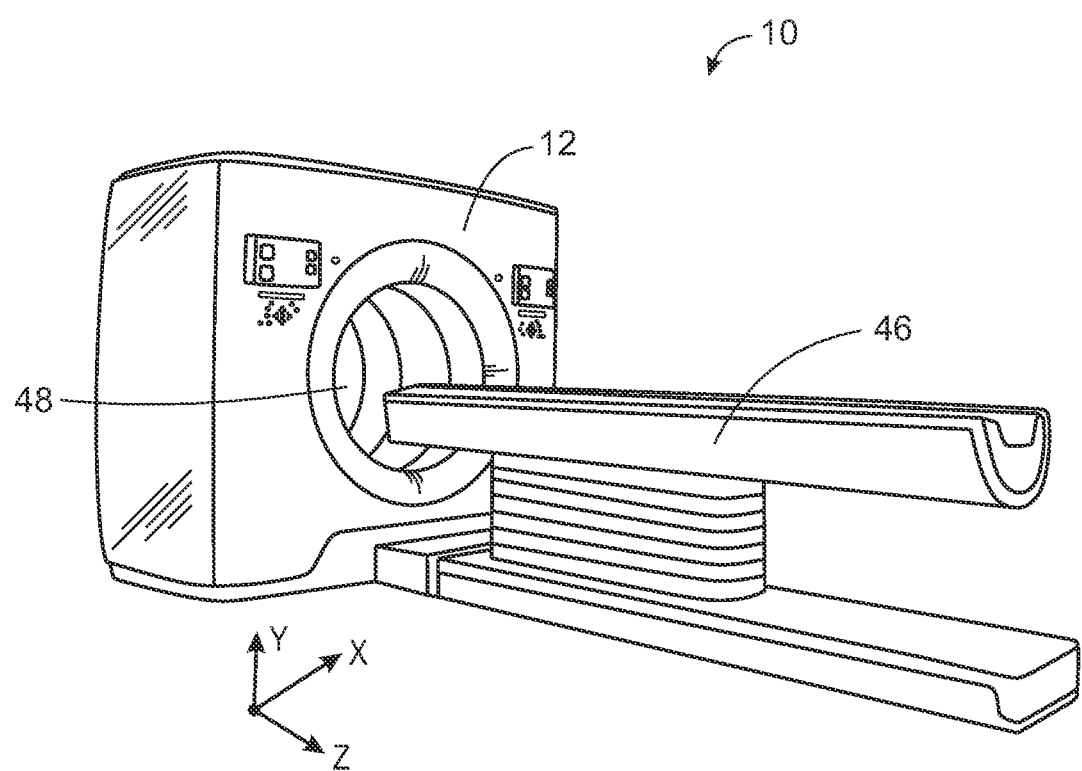
FIG. 1 shows a pictorial view of a computed tomography (CT) imaging system.
Figure 2:
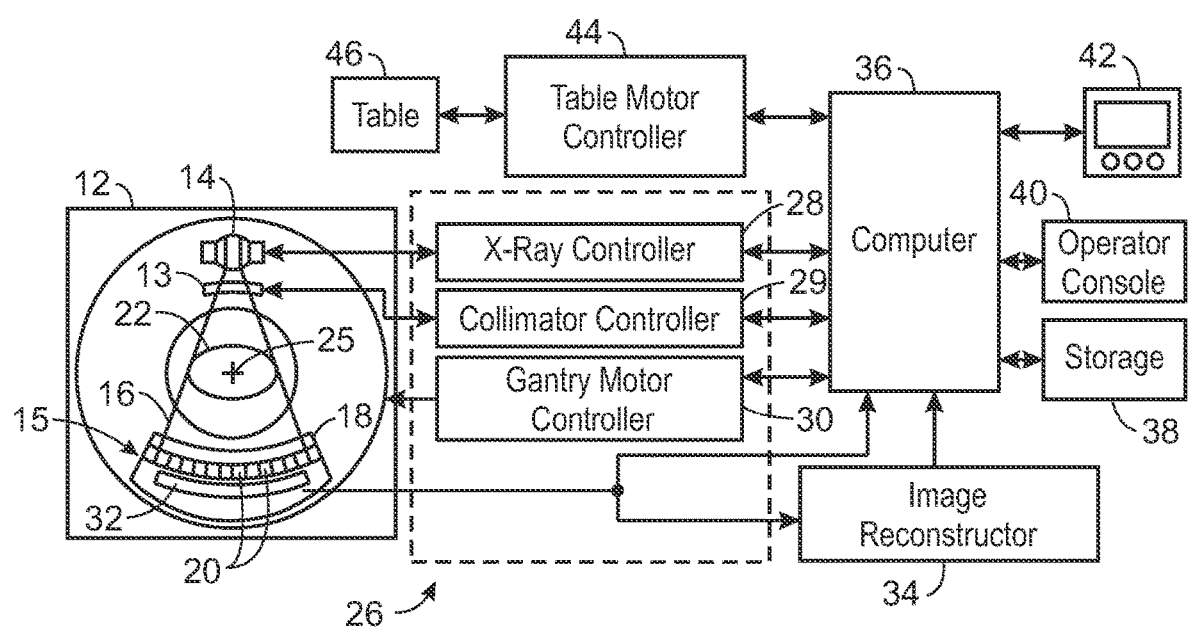
FIG. 2 shows a block schematic diagram of an example CT imaging system.
Figure 3:
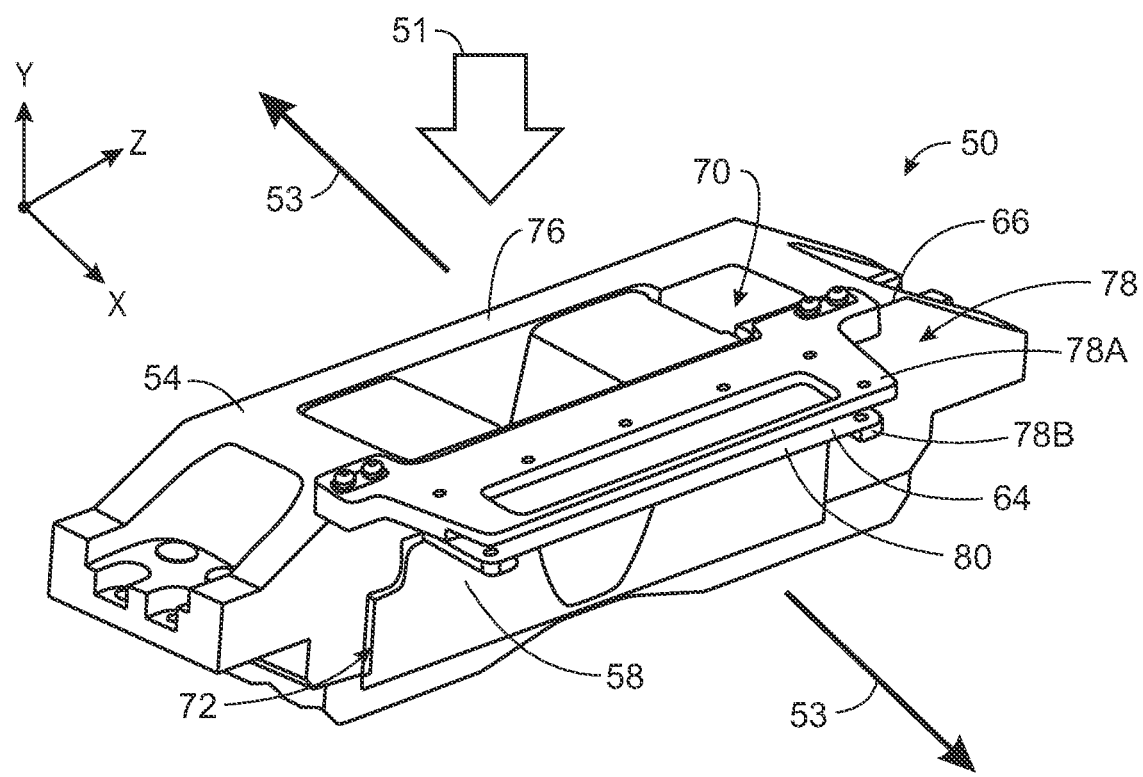
FIG. 3 shows a perspective view of an example integrated filter assembly including a carriage, a beam hardening filter, and a bowtie filter.
Figure 4:
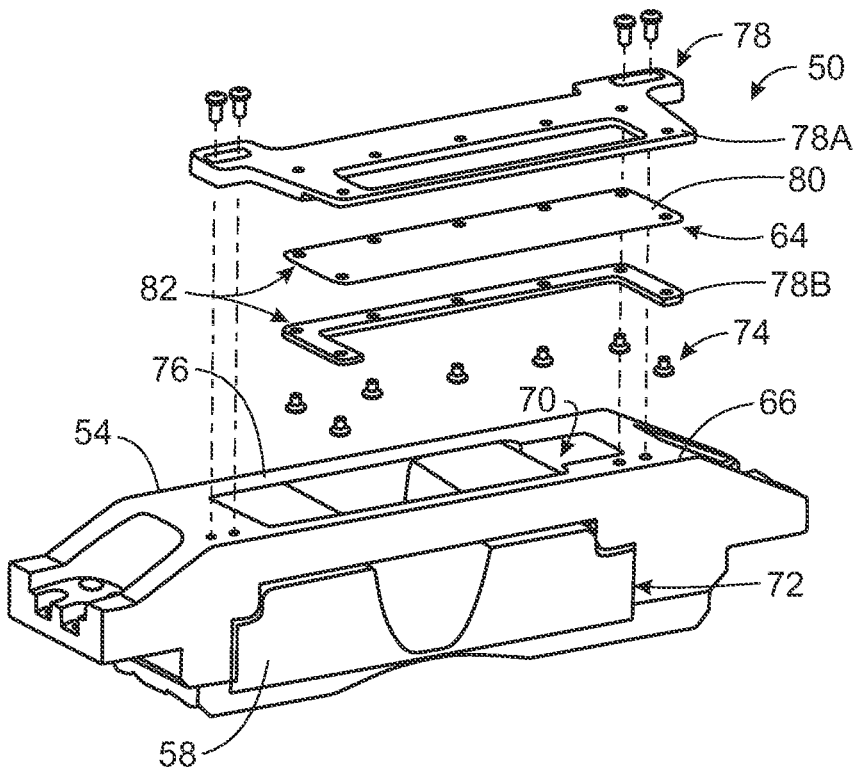
FIG. 4 shows a first partial exploded view of the example integrated filter assembly of FIG. 3.
Figure 5:
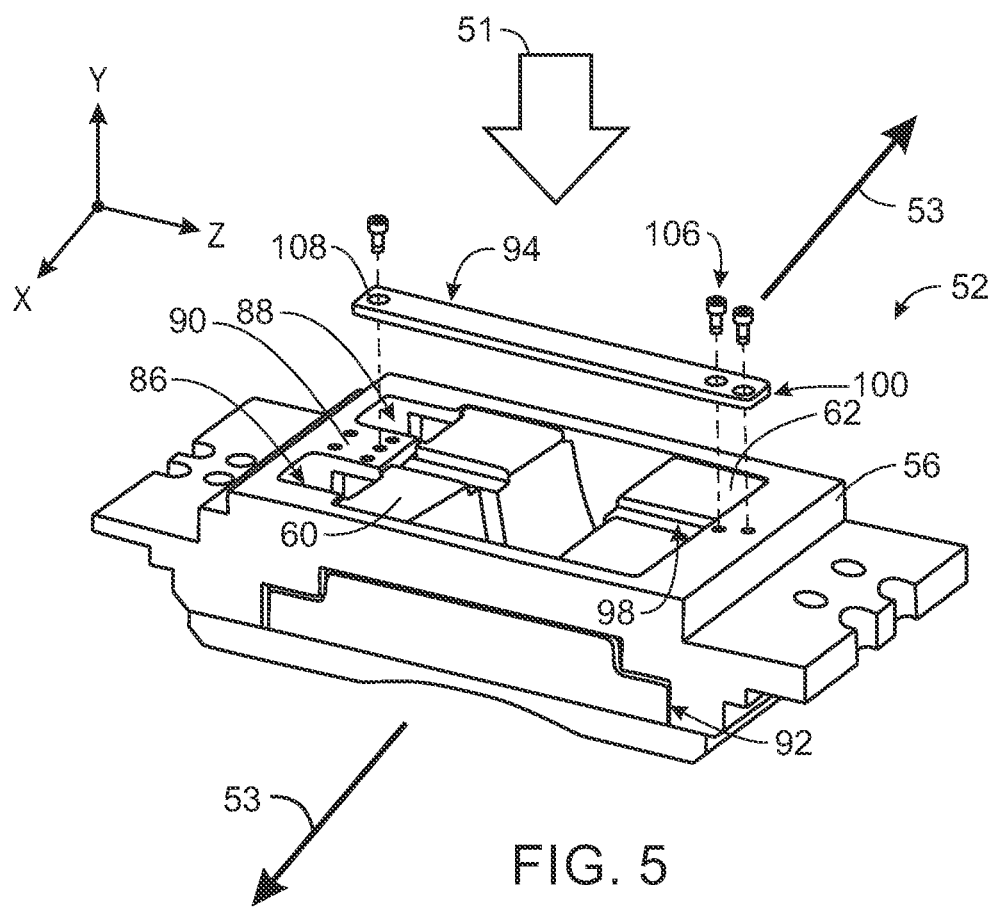
FIG. 5 shows a partial exploded view of an example integrated filter assembly, including a carriage and at least two bowtie filters.
Figure 6:
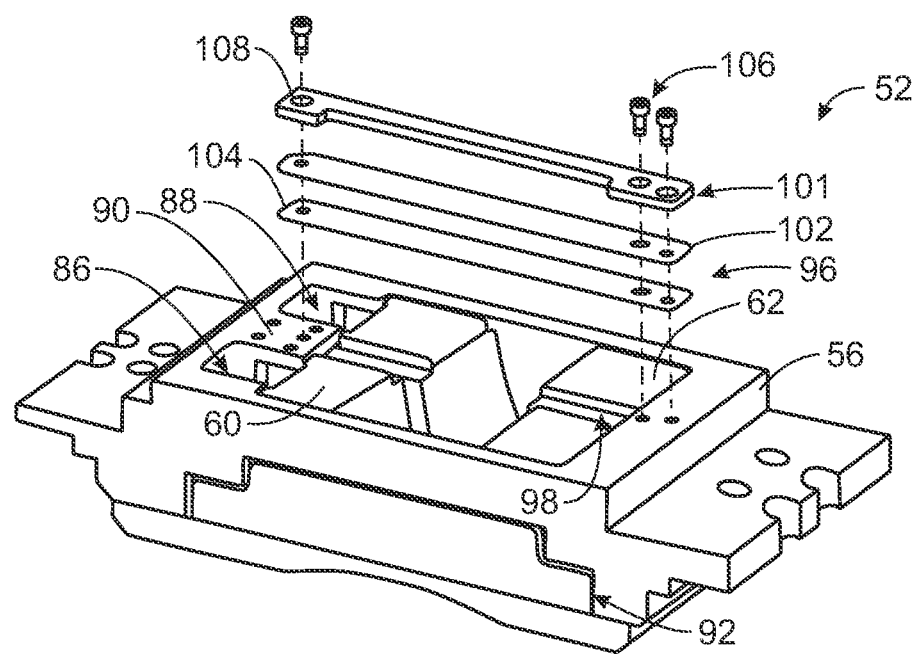
FIG. 6 shows a partial exploded view of an example integrated filter assembly including a carriage and at least two bowtie filters.
Figure 7A:
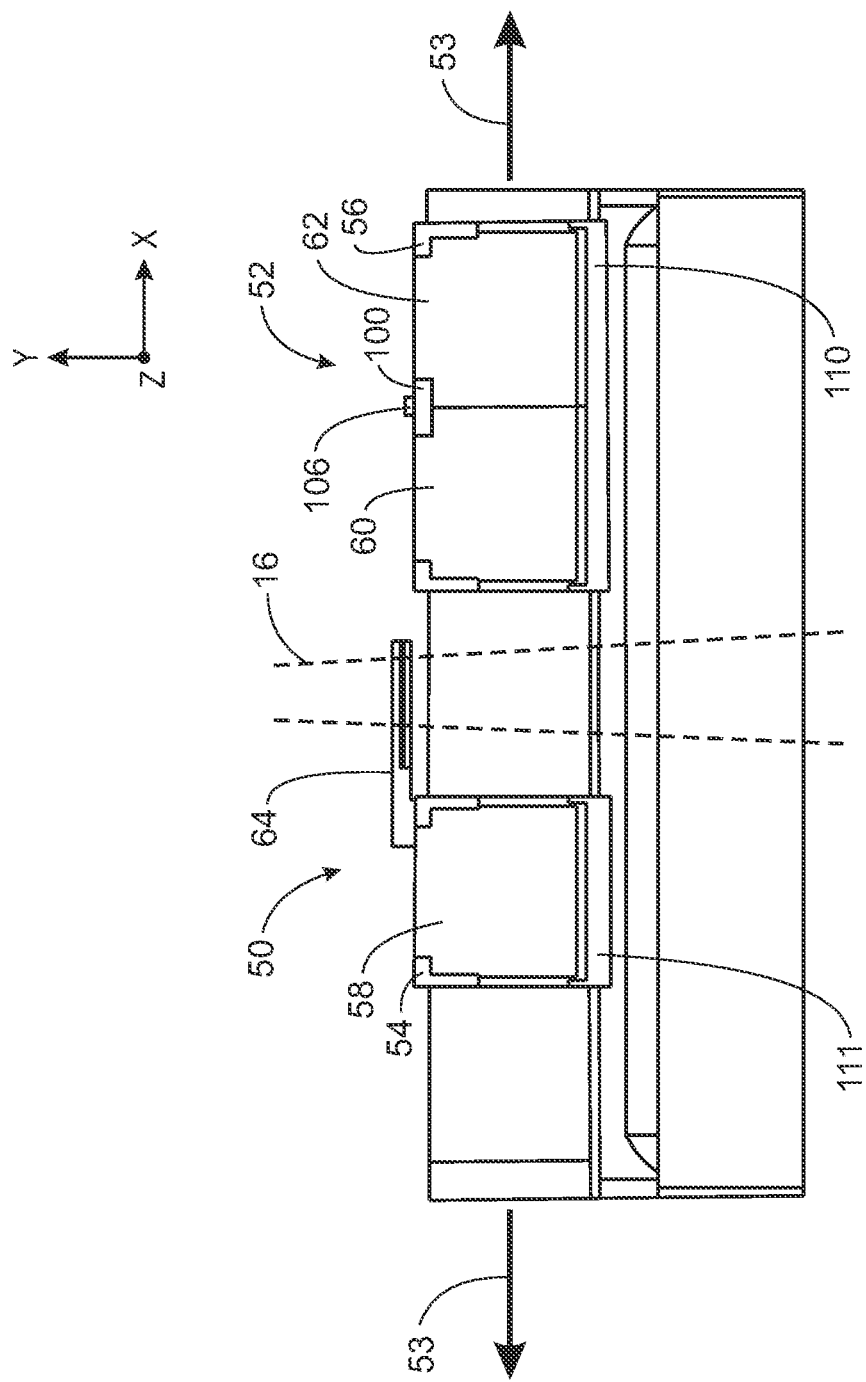
FIGS. 7A and 7B show cross-sectional views of an example collimator assembly including the integrated filter assembly of FIGS. 3-4 and the integrated filter assembly of FIG. 5 in different positions within the collimator assembly.
Figure 7B:
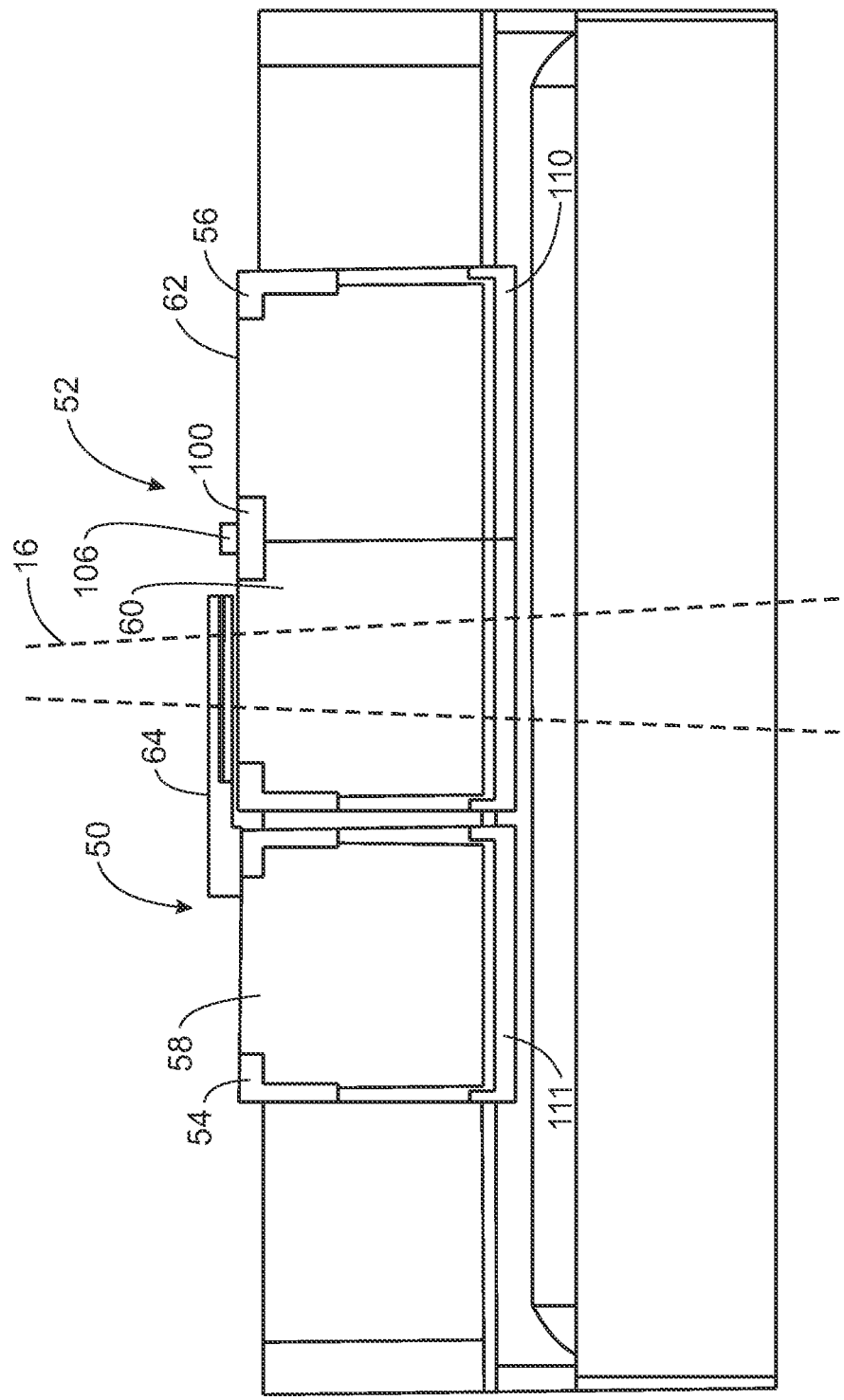
Figure 8:
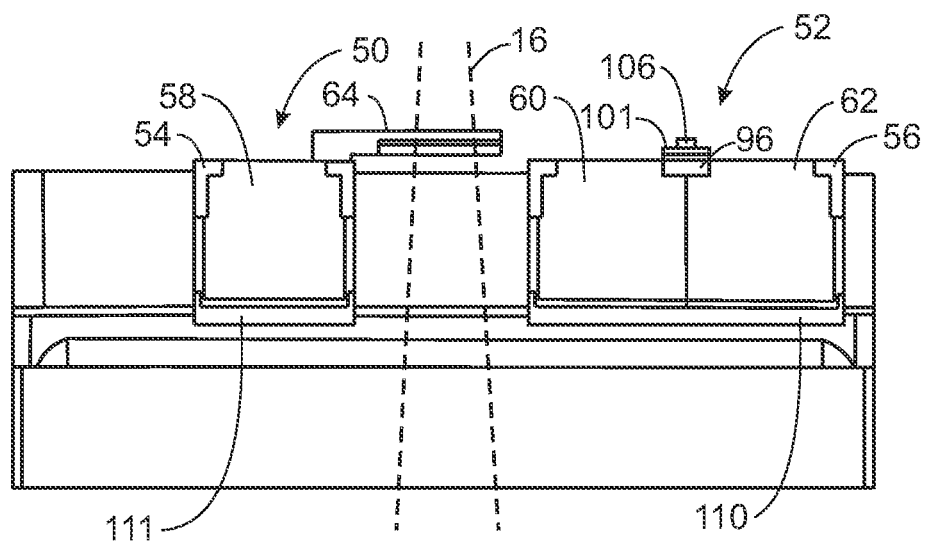
FIG. 8 shows a cross-sectional view of an alternative example collimator assembly including integrated filter assembly of FIGS. 3-4 and the integrated filter assembly of FIG. 6.
Figure 9:
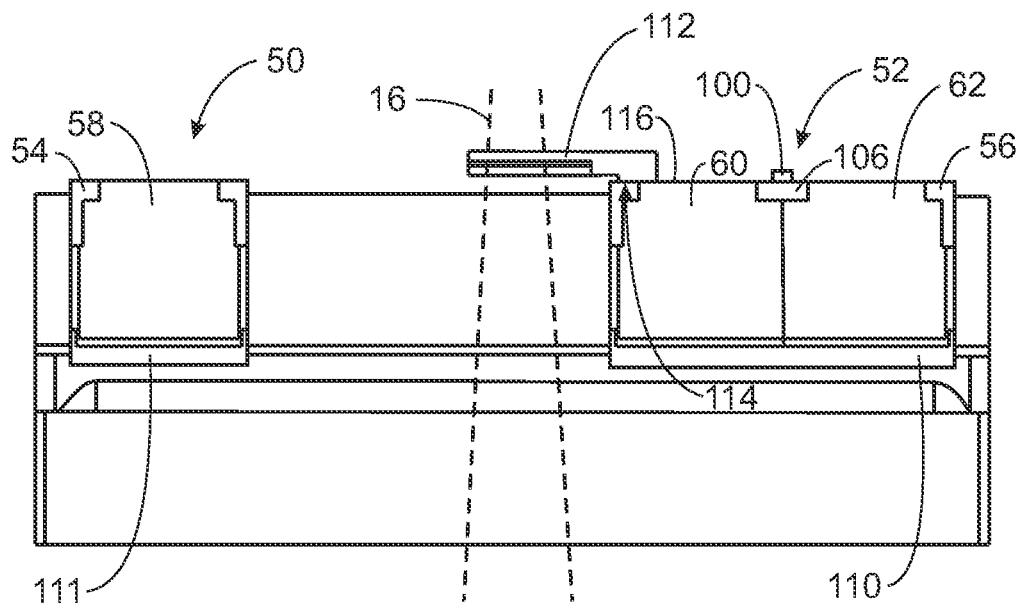
FIG. 9 shows a cross-sectional view of another alternative example collimator assembly including alternative example integrated filter assemblies.
Figure 10:
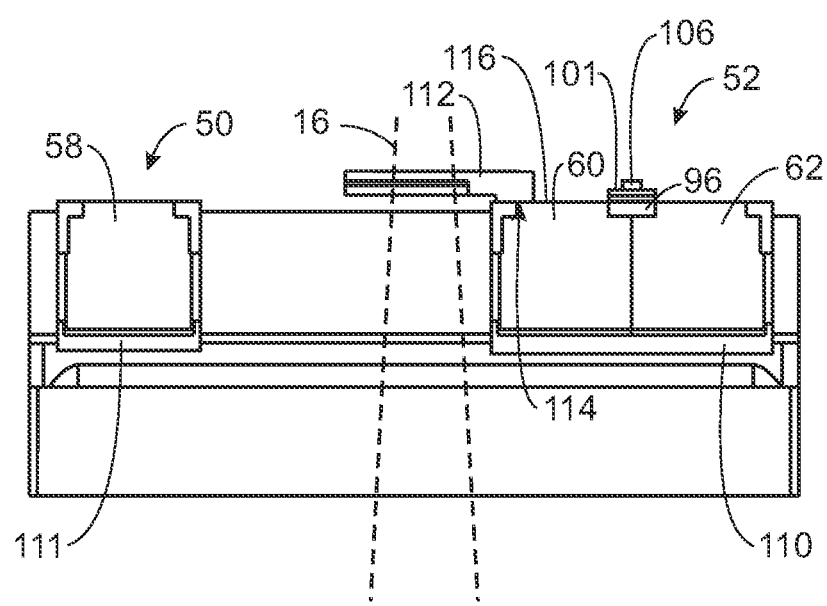
FIG. 10 shows a cross-sectional view of another alternative example collimator assembly including alternative example integrated filter assemblies.
Figure 12B:
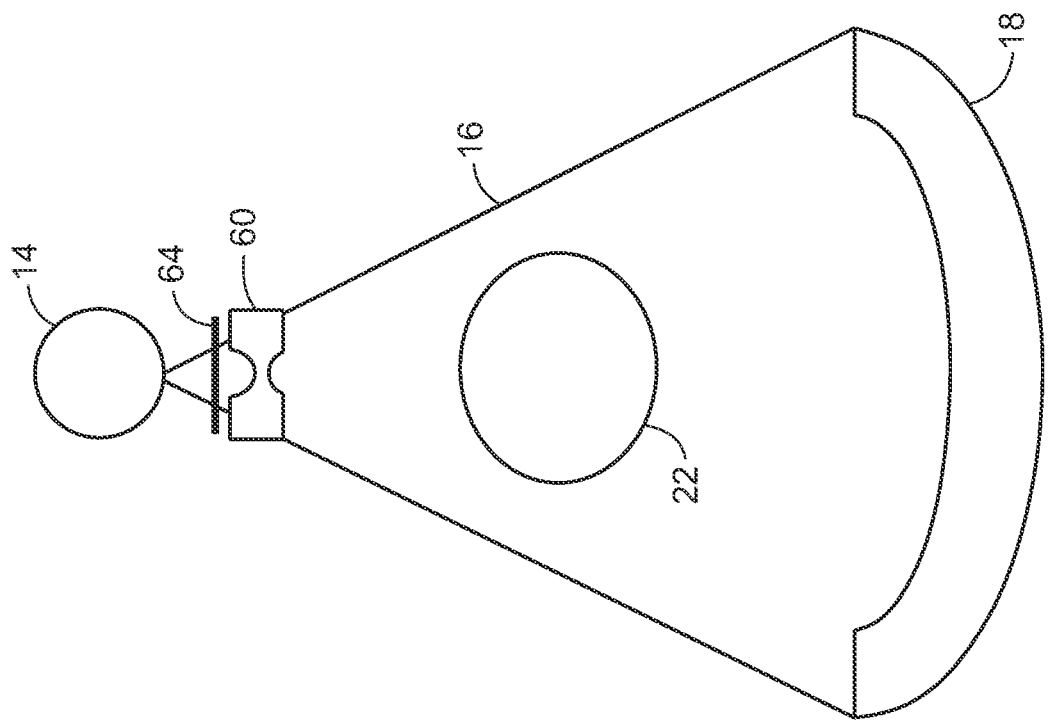
FIG. 12B shows a schematic diagram illustrating components of a scan using the example filter assembly in the fifth position shown in FIG. 11E.
Figure 12A:
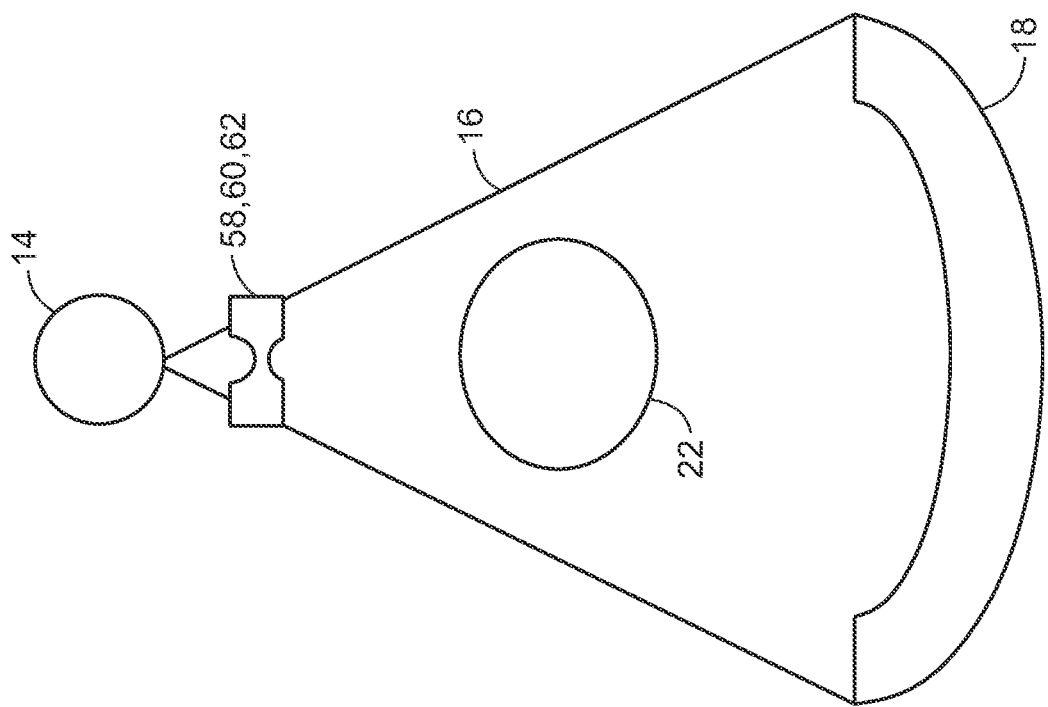
FIG. 12A shows a schematic diagram illustrating components of a scan using the example filter assembly in one of the second, third, or sixth positions shown in FIGS. 11B, 11C, and 11F.
Figure 12C:
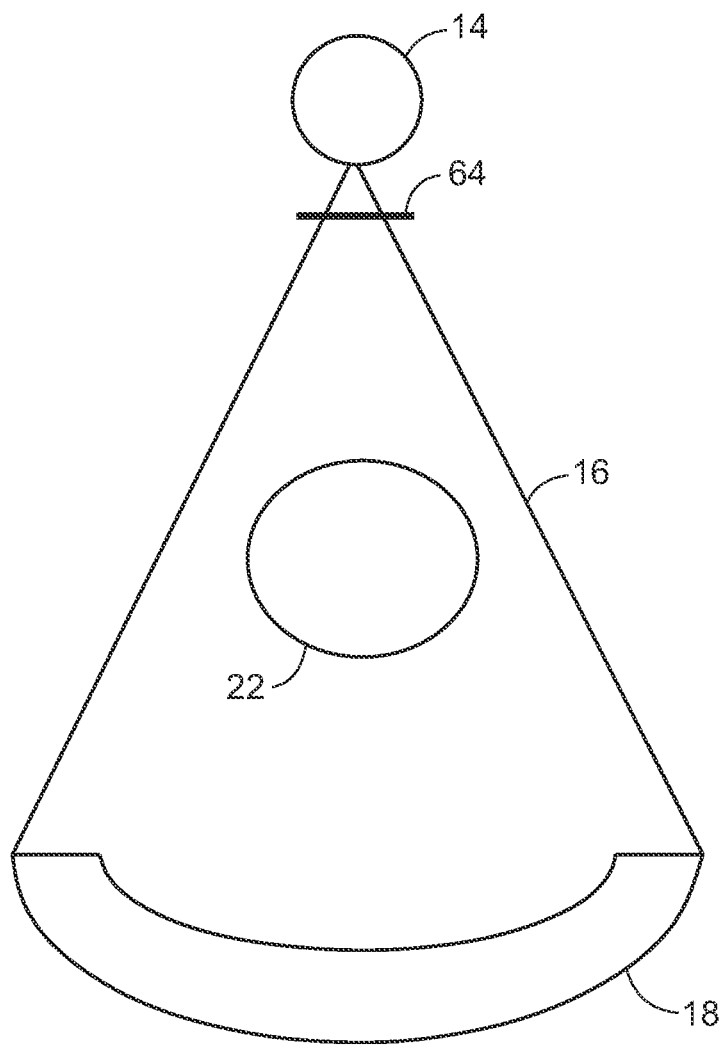
FIG. 12C shows a schematic diagram illustrating components of a scan using the example filter assembly in the fourth position shown in FIG. 11D.
Figure 13:
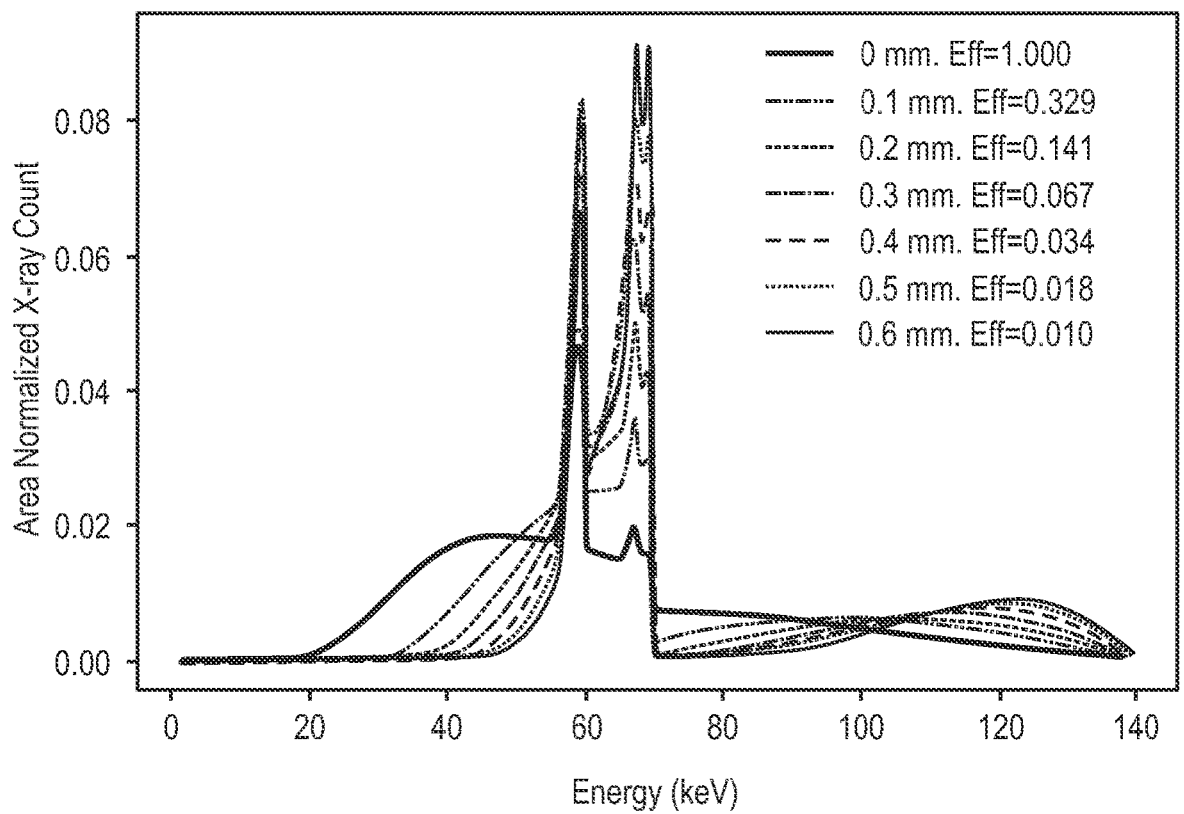
FIG. 13 shows example energy spectrum curves for different beam hardening filters that may be used with the example filter assembly described herein.
Figure 14:
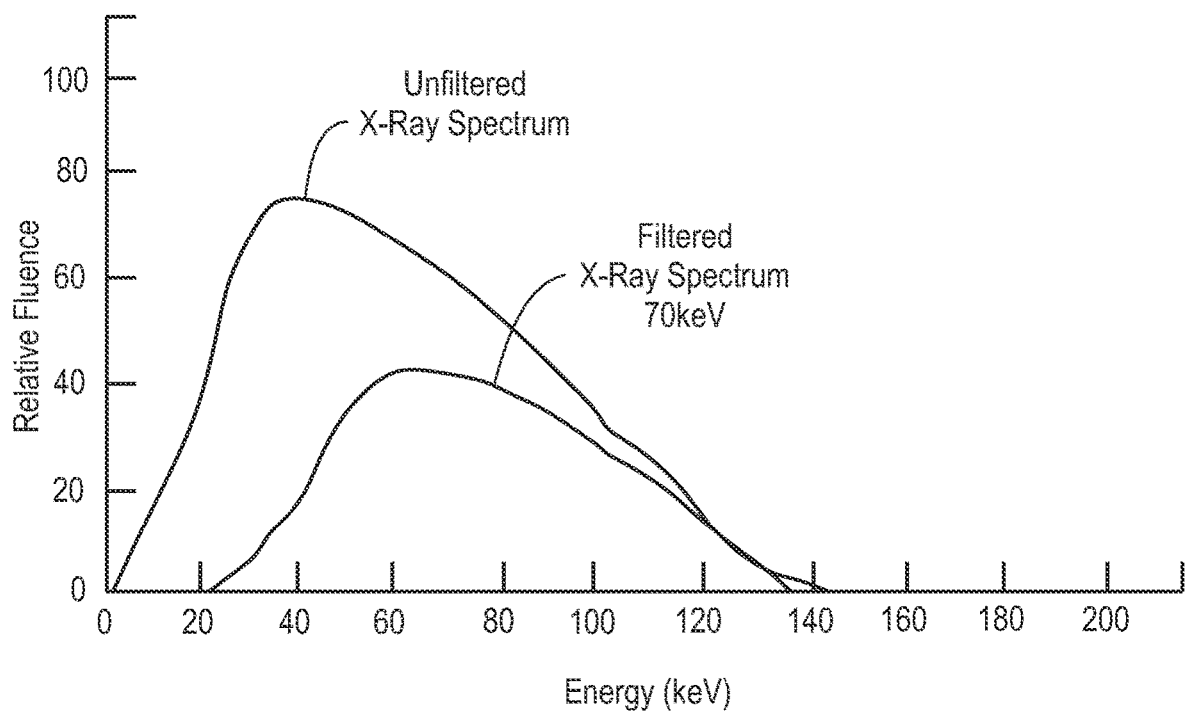
FIG. 14 shows a comparison between the energy spectrum of unfiltered X-rays and filtered X-rays.
Figure 15:
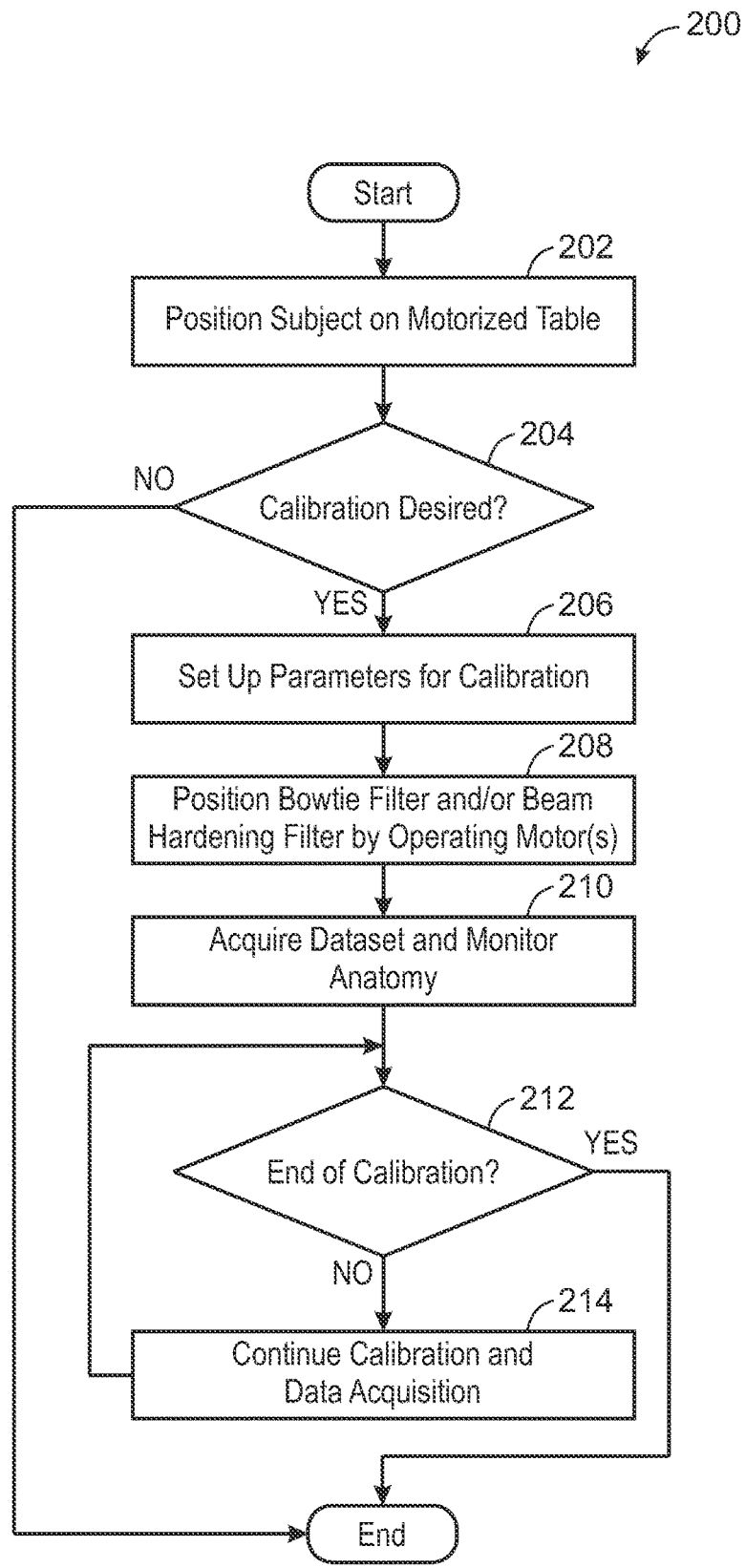
FIG. 15 shows a flow chart of an example method for calibration using the integrated filter assembly.
Figure 16:
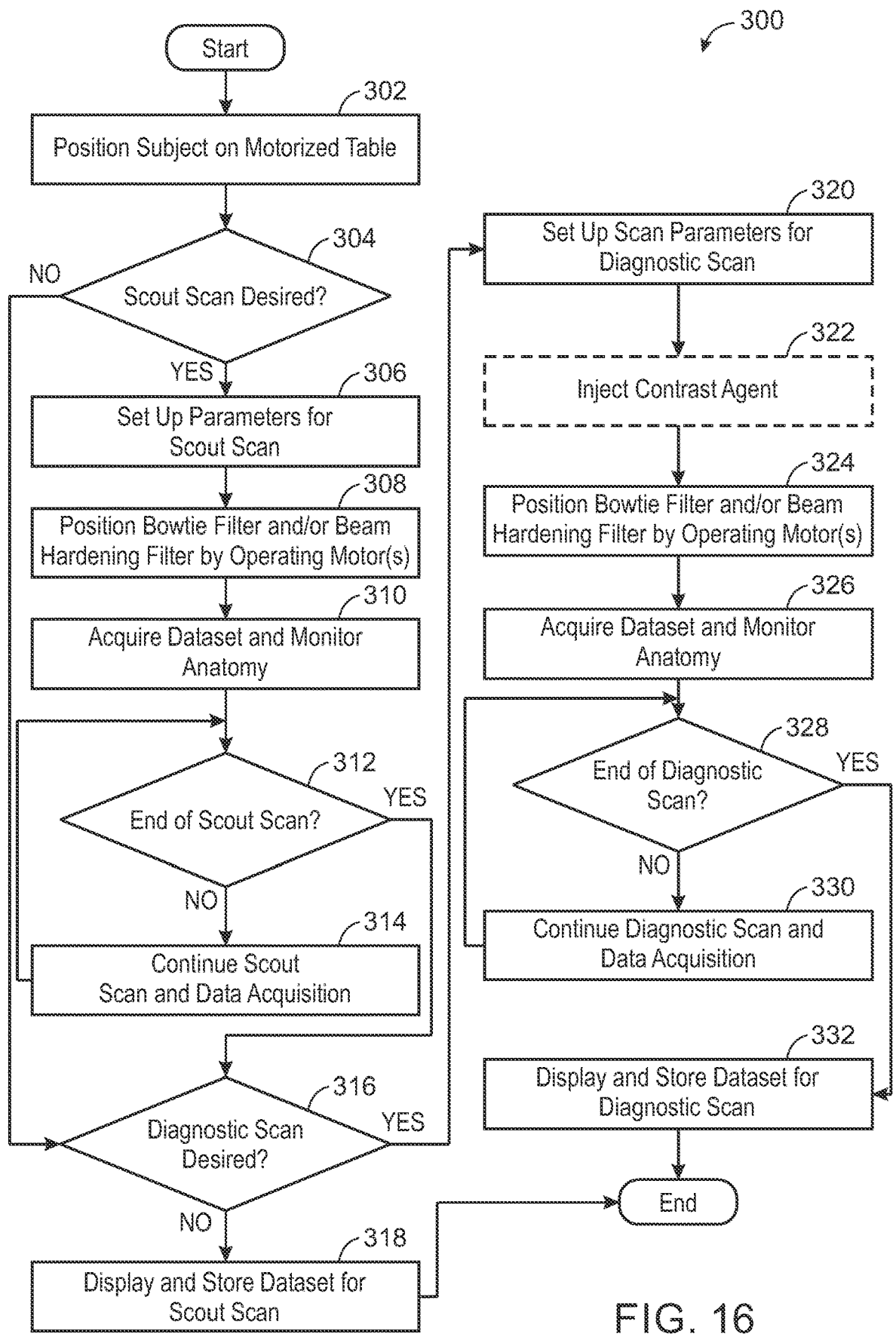
FIG. 16 shows a flow chart of an example method for scout and diagnostic scanning using the integrated filter assembly.

The following description relates to various embodiments of an X-ray imaging systems and methods. In particular, systems and methods are provided for a computed tomography (CT) imaging system using at least one beam hardening filter and at least one bowtie filter. FIGS. 1-2 show an example embodiment of a computed tomography (CT) imaging system, wherein the one or more filters are positioned between an X-ray source, e.g., an X-ray tube, and the imaging subject. Different filters may be selected based on the anatomy of the subject being imaged or for calibration. FIGS. 3-4 shows an example of an integrated filter assembly including a carriage, a beam hardening filter, and a bowtie filter, which may be positioned to adjust a spatial distribution and condition the beam reaching the subject. As an example, in a single carriage, a bowtie filter may be positioned adjacent to a beam hardening filter that is coupled to one edge of the carriage. The bowtie filter or the beam hardening filter may be positioned in a path of the beam by moving the carriage along an axis perpendicular to the beam. FIG. 5 shows an example second carriage including two bowtie filters that may be used in conjunction with the first carriage. FIG. 6 shows an example second carriage including two bowtie filters and an optional beam hardening filter that may be used in conjunction with the first carriage. The second carriage may be positioned such that a filter of the second carriage is positioned in the path of the beam simultaneously with the beam hardening filter of the first carriage. FIGS. 7A-7B show cross-sectional views of different positions of the example first and second carriages. FIGS. 8-10 depict different configurations of first and second carriages including different beam hardening filter positions. For example, the beam hardening filter may be coupled to the second carriage (e.g., the carriage with two bowtie filters). FIGS. 11A-11F show various positions of an example filter assembly with three bowtie filters and a beam hardening filter. FIGS. 12A-12C are schematic diagrams illustrating various components of scans that may be implemented using the example filter assembly. For example, the beam hardening filter may be used for a low-dose scan and/or for calibration of the CT imaging system. FIGS. 13 and 14 graphically represent the reduced dose and energy spectrum when using the example filter assembly. FIG. 15 shows an example method for calibrating an imaging system using one or more filters included in the integrated filter assembly. FIG. 16 shows an example method for imaging a subject using one or more filters included in the integrated filter assembly.

Though a CT imaging system is described by way of example, it may be understood that the present techniques may also be useful when applied to images acquired using other imaging modalities, such as X-ray imaging systems, fluoroscopy imaging systems, interventional imaging systems, mammography imaging systems, surgical imaging systems, and so forth. The present discussion of a CT imaging modality is provided merely as an example of one suitable imaging modality.

Various embodiments may be implemented in connection with different types of imaging systems. For example, various embodiments may be implemented in connection with a CT imaging system in which an X-ray source projects a fan- or cone-shaped beam that is collimated to lie within an x-y plane of a Cartesian coordinate system and generally referred to as an "imaging plane." The X-ray beam passes through a subject being imaged, such as a patient. The X-ray beam, after being attenuated by the patient, impinges upon an X-ray detector. The intensity of the attenuated X-ray beam received at the X-ray detector is dependent upon the attenuation of an X-ray beam by the imaging subject. Each detector element of the X-ray detector produces a separate electrical signal that is a measurement of the X-ray intensity at each detector element location. The X-ray intensity measurements from all of the detector elements are acquired separately to produce a transmission profile.

In a typical rotating CT imaging system, the X-ray source and the X-ray detector are rotated within a gantry around a subject to be imaged such that the angle at which the X-ray beam intersects the imaging subject constantly changes. A complete gantry rotation occurs when the gantry concludes one full 360-degree revolution. A group of X-ray attenuation measurements (e.g., projection data) from the X-ray detector at one gantry angle is referred to as a "view." A view is, therefore, each incremental position of the gantry. A "scan" of the subject comprises a set of views made at different gantry angles, or view angles, during one revolution of the X-ray source and X-ray detector. In an axial diagnostic scan, the projection data is processed to construct an image that corresponds to a two-dimensional slice taken through the subject. A scout scan (also referred herein as localizer scan) provides a projection view along a longitudinal axis of the imaging subject and generally provides aggregations each including internal structures of the subject. One method for reconstructing an image from a set of projection data is referred to in the art as a filtered back projection technique. This process converts the attenuation measurements from a scan into integers called "CT numbers" or "Hounsfield units" (HU), which are used to control the brightness of a corresponding pixel on a display.

X-ray beam characteristics such as size, shape, and energy may be different for a scout scan (also referred herein as localizer scan) and a diagnostic scan. During certain scout scans and diagnostic scans, it is desired to use higher power X-rays. The higher power X-rays improve the image quality of the diagnostic scan and increases thermal stability of the X-ray source. However, an increase in X-ray power, may increase the X-ray radiation exposure or dose for a patient. The beam hardening filter may be used in the path of the X-ray beam to attenuate the X-rays and reduce the amount of a lower energy X-ray beam prior to it entering the patient's body (FIG. 14). The beam hardening filter along with a bowtie filter may be used when a higher energy X-ray beam is desired for a patient scan, for example, a large patient. The beam hardening filter and the bowtie filters may be mounted on separate carriages which can be moved in and out of the X-ray beam as desired. However, adding multiple carriages will add cost and complexity to the pre-patient collimator assembly. Also, the time to complete scans may be longer due to moving carriages in and out of the X-ray beam between sections of a scan. Therefore, according to embodiments disclosed herein, a single integrated filter assembly may in incorporated including a carriage, a plurality of beam hardening filters, and a plurality of bowtie filters. Based on the scan setup, one or more filters from the carriage may be placed in the path of the X-ray beam. By including multiple bowtie and beam hardening filters in a single integrated filter assembly, reliability of the set up may be increased while cost and complexity of the setup may be decreased.

FIG. 1 illustrates an exemplary computed tomography (CT) imaging system 10 and FIG. 2 depicts an example block diagram of the exemplary CT imaging system according to an embodiment. The CT imaging system includes a gantry 12. The gantry 12 has an X-ray source 14 that generates and projects a beam of X-rays 16 toward an X-ray detector assembly 15 on the opposite side of the gantry 12. The X-ray source 14 projects the beam of X-rays 16 through a pre-patient collimator assembly 13 that conditions the beam of X-rays 16 using, for example, one or more filters. The X-ray detector assembly 15 includes a collimator assembly 18 (a post-patient collimator assembly), a plurality of detector modules 20 (e.g., detector elements or sensors), and data acquisition systems (DAS) 32. The plurality of detector modules 20 detect the projected X-rays that pass through a subject or subject 22 being imaged, and DAS 32 converts the data into digital signals for subsequent processing. Each detector module 20 in a conventional system produces an analog electrical signal that represents the intensity of an incident X-ray beam and hence the attenuated beam as it passes through the subject 22. During a scan to acquire X-ray projection data, gantry 12 and the components mounted thereon rotate about a center of rotation 25 (e.g., isocenter) so as to collect attenuation data from a plurality of view angles relative to the imaged volume.

Rotation of gantry 12 and the operation of X-ray source 14 are governed by a control system 26 of CT imaging system 10. Control system 26 includes an X-ray controller 28 that provides power and timing signals to an X-ray source 14, a collimator controller 29 that controls a length and a width of an aperture of the pre-patient collimator assembly 13 (and, thus, the size and shape of the beam of X-rays (e.g., X-ray beam) 16), and a gantry motor controller 30 that controls the rotational speed and position of gantry 12. An image reconstructor 34 receives sampled and digitized X-ray data from DAS 32 and performs high-speed image reconstruction. The reconstructed image is applied as an input to a computer 36, which stores the image in a storage device 38. Computer 36 also receives commands and scanning parameters from an operator via an operator console 40. An associated display 42 allows the operator to observe the reconstructed image and other data from computer 36. The operator supplied commands and parameters are used by computer 36 to provide control signals and information to DAS 32, X-ray controller 28, collimator controller 29, and gantry motor controller 30. In addition, computer 36 operates a table motor controller 44, which controls a motorized table 46 to position subject 22 and gantry 12. Particularly, table 46 moves portions of subject 22 through a gantry opening or bore 48.

In accordance with aspects of the present disclosure, the CT imaging system 10 is configured to perform automatic exposure control responsive to user input. Exposure control may be achieved using one or more filter assemblies (e.g., filter assemblies 50 and 52 of FIGS. 3-6) that may be mounted within gantry 12 between X-ray source 14 and the subject 22. The filter assemblies 50, 52 may travel in and out of the beam 16 in the z-direction while the beam 16 is substantially in the y-direction. In the example described herein, the filter assemblies 50, 52 include multiple bowtie filters and at least one beam hardening filter. The filter assemblies 50, 52 may be positioned such that more than one filter may be positioned in the path of the X-ray beam 16 during a scan.

FIGS. 3-6 depict example filter assemblies 50, 52 that may be used with the example CT imaging system 10 described herein. The two filter assemblies 50, 52 may each include a carriage 54, 56, and each carriage 54, 56 may include at least one bowtie filter. Combined, the filter assemblies 50, 52 include multiple different bowtie filters. In particular, the first filter assembly 50 depicted in FIGS. 3-4 includes a first carriage 54 having a first bowtie filter 58. The second filter assembly 52 depicted in FIGS. 5-6 includes a second carriage 56 having a second bowtie filter 60 and a third bowtie filter 62. Additionally, the example carriages 54, 56 may include a beam hardening filter. In the illustrated examples of FIGS. 3, 4 and 6, the first carriage 54 includes a first beam hardening filter 64 that extends from a top edge 66 of the carriage 54 and the second carriage 56 includes a second beam hardening filter 96 positioned between the second and third bowtie filters 60, 62 as shown in FIG. 6. However, the beam hardening filters 64, 96 may be configured differently (e.g., as depicted in alternative constructions in FIGS. 8-10). The bowtie filters 58, 60, 62 are shown here in rectangular shape as an example. Each bowtie filter 58, 60, 62 may be rigid and non-deformable. The bowtie filters 58, 60, 62 may alternatively have different shapes and material constructions to provide the proper X-ray spectrum for imaging various types of anatomies. The bowtie filters 58, 60, 62 may change the spatial distribution of the X-ray beam (i.e., condition the X-ray beam) in the axial plane of the subject 22, such as a patient. For example, the redistributed X-ray beam 16 may have higher energy at the center and lower energy at the periphery of the subject 22. Each of the bowtie filters 58, 60, 62 may be designed to image a specific anatomy or section of the human body, such as head, chest, and abdomen. During imaging, one of the bowtie filters 58, 60, 62 may be selected based on the anatomy of the subject 22 to be scanned, and the selected filter may be placed into the X-ray beam path 16. Responsive to a change in the anatomy, the filter(s) may be changed from one to another. Based on a nature of the scan, the carriage(s) may be positioned such that a beam hardening filter may or may not be placed in the X-ray beam path 16. The beam hardening filters) 64, 96 may attenuate the X-ray beam 16 and remove low energy components thereby conditioning the X-ray beam 16 for specific scans, such as a patient scan or a calibration scan.

The first filter assembly 50 is shown in FIGS. 3-4. The first filter assembly 50 may include a first carriage 54. The first carriage 54 may include a first slot 70 formed lengthwise within a cavity of the first carriage 54. In one example, the first slot 70 may extend through the entire length of the first carriage 54. In another example, the first slot 70 may partially extend through the length of the first carriage 54.

A first bowtie filter 58 may be housed within the first slot 70. The first bowtie filter 58 may be shaped as a "bowtie" with a first, straight long side and a second, parallel long side including a central ridge. The first bowtie filter 58 may be formed of graphite. A bowtie filter 58 may be used to adjust spatial distribution of an X-ray beam 51 passing through the first bowtie filter 58 and the size of the bowtie filter governs a level of spatial distribution adjustments made to the X-ray beam 16 passing through the first bowtie filter 58. The carriage 54 may include a cut-out 72 on a side wall through which the bowtie filter 58 may be visible. The first carriage 54 may be moved along a direction perpendicular to the X-ray beam 51 as shown by arrows 53 to position the X-ray beam on the bowtie filter 58 or a beam hardening filter 64.

A beam hardening filter 64 may be coupled to the carriage 54 on an edge 66 of a top surface 76 of the carriage 54. The beam hardening filter 64 may be positioned adjacent to the first bowtie filter 58 and extends away from the edge 66 of the carriage 54 and the first bowtie filter 58. The physical sizing of the beam hardening filter 64 may vary but may be equal to or smaller than the physical size of the first bowtie filter 58 due to the proximity of the beam hardening filter 64 which is closer to the X-ray source 14 than filter 58. As the beam hardening filter 64 is positioned extending from a top surface 76 of the first carriage 54, the first and second carriages 54, 56 may be positioned such that the beam hardening filter 64 overlaps (e.g., extends over) a bowtie filter (e.g., the second bowtie filter 60 or the third bowtie filter 62) in the second carriage 56.

The beam hardening filter 64 may include a support structure 78, and one or more metal sheets 80 sandwiched between the support structure 78. In this example, the support structure 78 includes a top window frame member 78A and a bottom support member 78B on either side of the one or more metal sheets 80. Each metal sheet 80 and the support structure 78 may be stacked together and fastened at the edge 66 of the carriage 54 via a plurality of fasteners 74. In this example, a plurality of concentric holes 82 are formed in the metal sheet 80 and the support structure 78, and each fastener 74 (used to attach the layers of the beam hardening filter 64 to the carriage 54) may pass through each of the concentric holes 82 present in each layer. In one example, the support structure 78 may be made of a metal such as aluminum, and the metal sheet 80 may be made of the same metal or different metals. Examples of high attenuating materials or heavy element materials for the metal sheet 80 include copper, lead, tin, molybdenum, tungsten, titanium, zirconium, etc. The metal sheet 80 filters low energy X-rays out and keeps high energy X-rays as shown in FIG. 14. Alternatively, when a specific energy threshold is necessary in the X-ray detector, the beam hardening filter 64 may be tungsten and used primarily for calibrating the X-ray detector. This is especially true for a photon counting X-ray detector of a photon counting CT imaging system that has a plurality of energy thresholds to allocate each captured X-ray to a plurality of energy bins, for example, a plurality of low, medium, and high energy bins. The energy binning enables material identification in patient images that enhances CT diagnostic capability. The calibration of energy thresholds in the X-ray detector can be achieved by a mono-energy X-ray source. While a thin tungsten film (<50 um) can act as a typical beam hardening filter, a thick tungsten of 200 um~600 um absorbs most of poly-energetic X-ray source output and emits tungsten specific K-edge X-ray of 69.5 keV (FIG. 13). Other heavy element materials, like lead, emit their own specific K-edge X-ray energy and can be used as a mono-energy source as well. 300 um thick tungsten prevents more than 99% of the X-ray beam from penetrating the filter, resulting in a single energy X-ray at the specific energy of 69.5 keV (FIG. 13). The specific energy that is emitted from a tungsten beam hardening filter is ideal for calibrating the energy thresholds for a photon counting X-ray detector of a photon counting CT imaging system.

The beam hardening filter 64 may be used to intercept lower energy X-rays, thereby attenuating, and "hardening" the X-ray beam 51 passing through the beam hardening filter 64. The degree of X-ray beam attenuation may depend on one or more of a number of attenuation layers (such as metallic sheets), the thickness of each attenuation layer, the materials used in the attenuation layers, and the overall size of the attenuation layers in the beam hardening filter.

As an example, when using thinner sheets of beam hardening material in the metal sheets 80, the support structure 78 may be used to limit deflection of the beam hardening filter 64 due to gantry rotational forces which may act to bend the middle of the beam hardening material. In this embodiment, the support structure 78 is positioned outside of the cross-sectional area of the hardened X-ray beam 51 that is used for imaging. In this way, the beam hardening filter 64 may be solely accounted for in hardening the X-ray beam 51 while being mechanically strengthened by the support structure 78 proximal to the area where the X-ray beam 51 passes through the beam hardening filter 64. Furthermore, the support structure 78 may be made from a stiff but lightweight material such as aluminum to minimize excess X-ray scatter near the beam hardening filter 64. The first filter assembly 50 may be used with the example CT imaging system 10 alone, or may be used with an additional filter assembly, such as the second filter assembly 52 of FIGS. 5-6.

The second filter assembly 52 is shown in FIGS. 5-6. The second filter assembly 52 may include a second carriage 56. The second carriage 56 may include a first slot 86 and a second slot 88 formed lengthwise within a cavity of the carriage 56. The first slot 86 may be separated from the second slot 88 via a tab 90. In one example, each of the two slots 86 and 88 may extend through the entire length of the second carriage 56. In another example, each of the two slots 86 and 88 may partially extend through the length of the carriage 56.

A second bowtie filter 60 may be housed within the first slot 86 while a third bowtie filter 62 may be housed in the second slot 88. In one example, the second bowtie filter 60 and the third bowtie filter 62 may be positioned next to each other but not in contact. In another example, the second bowtie filter 60 and the third bowtie filter 62 may be positioned next to each other in face-sharing contact. Each of the second bowtie filter 60 and the third bowtie filter 62 may be shaped as a "bowtie" with a first, straight long side and a second, parallel long side including a central ridge. In one example, the second bowtie filter 60 and the third bowtie filter 62 may be of the same size (such as width, length, thickness, etc.) In another example, the second bowtie filter 60 and the third bowtie filter 62 may be of different sizes (such as width, length, thickness). Each of the second bowtie filter 60 and the third bowtie filter 62 may be formed of graphite or other X-ray attenuating materials. A bowtie filter may be used to adjust spatial distribution of an X-ray beam 51 passing through the filter and the size of a bowtie filter governs a level of spatial distribution adjustments made to the X-ray beam 51 passing through the filter. The carriage 56 may include a cut-out 92 on a side wall through which a bowtie filter 60, 62 may be visible. As shown in this example, the third bowtie filter 62 may be co-planer with a side wall and cut-out 92 of the carriage 56. In FIG. 5, the bowtie filters 60, 62 may be secured within their respective slots 86, 88 via a support structure 100 and fasteners 106. The support structure 100 may be embedded in a recess 98 between the second bowtie filter 60 and the third bowtie filter 62 and secured at each end to the carriage 56 via the plurality of fasteners 106. In this example, a plurality of concentric openings 108 are formed on two ends of each of the support structure 100 and each fastener 106 (used to attach the support structure 100 to the carriage 56) may pass through each of the concentric openings 108. As an example, one end of the support structure 100 may be attached to the tab 90 of the carriage 56. The second carriage 56 may be moved along a direction perpendicular to the X-ray beam 51 as shown by arrows 53 to position the X-ray beam on one of the bowtie filters 60, 62.

FIG. 6 differs from FIG. 5, in that there is a beam hardening filter 96 that may be coupled to the carriage 56 in-between the second bowtie filter 60 and the third bowtie filter 62. The beam hardening filter 96 may be embedded in a recess 98 between the second bowtie filter 60 and the third bowtie filter 62. The length of the beam hardening filter 96 may be higher than or equal to the length of each of the second bowtie filter 60 and the third bowtie filter 62. However, the width of the beam hardening filter 96 may be narrower than the width of each of the second bowtie filter 60 and the third bowtie filter 62. As the beam hardening filter 96 is positioned between the second bowtie filter 60 and the third bowtie filter 62, the beam hardening filter 96 may at least partly overlap with each of the second bowtie filter 60 and the third bowtie filter 62 and may be in face sharing contact with the top/side surfaces of the bowtie filters.

The beam hardening filter 96 may include one or more metal strips 102, 104 underneath a support structure 101. In this example, a first metal strip 102 and a second metal strip 104 may be positioned under the support structure 101. Each of the first metal strip 102, the second metal strip 104, and the support structure 101 may be stacked together and secured at each end to the carriage 56 via a plurality of fasteners 106. In this example, a plurality of concentric openings 108 are formed on two ends of each of the first metal strip 102, the second metal strip 104, and the support structure 101 and each fastener 106 (used to attach the layers of the beam hardening filter 96 to the carriage 56) may pass through each of the concentric openings 108 present in each layer. As an example, one end of the beam hardening filter 96 may be attached to the tab 90 of the carriage 56. In one example, the support structure 101 may be made of a metal such as aluminum, and first metal strip 102 and the second metal strip 104 may be made of a same metal or different metals. Examples of high attenuating materials or heavy element materials for the metal strips 102,104 include copper, lead, tin, molybdenum, tungsten, titanium, zirconium, etc.

The beam hardening filter 96 may be used to absorb lower energy X-rays, thereby attenuating low energy X-rays, and "hardening" the X-ray beam 51 passing through the beam hardening filter 96. The degree of beam attenuation may depend on one or more of a number of attenuation layers (such as metal strips), the thickness of each attenuation layer, the materials used in the attenuation layers, and the overall size of the attenuation layers. The degree of beam attenuation is much higher with heavy element materials (high attenuating materials). Heavy element materials, like tungsten, absorb incoming X-rays and emits their unique K-edge x-ray that is of a mono-energy. A mono-energy X-ray beam is mainly intended for X-ray detector energy threshold calibration.

As an example, when using thinner strips of beam hardening material in the metal strips 102, 104, the support structure 101 may be used to limit deflection due to gantry rotational forces which may act to bend the middle of the beam hardening material. In this embodiment, the support structure 101 is positioned outside of the cross-sectional area of the hardened X-ray beam 51 that is used for imaging. In this way, the beam hardening filter 96 may be solely accounted for in hardening the X-ray beam 51 while being mechanically strengthened by the support structure 101 proximal to the area where the X-ray beam 51 passes through the beam hardening filter 96. Furthermore, the support structure 101 may be made from a stiff but lightweight material such as aluminum to minimize excess X-ray scatter near the beam hardening filter.

FIGS. 7A and 7B illustrate cross-sectional views of a first integrated filter assembly 50 of FIGS. 3-4 and a second integrated filter assembly 52 of FIG. 5 positioned within the example CT imaging system 10 of FIG. 1. As depicted in FIGS. 7A and 7B, the filter assemblies 50, 52 may be positioned such that the first beam hardening filter 64 of the first filter assembly 50 is positioned in the path of the X-ray beam 16. In this position, the beam hardening filter 64 is the only filter positioned in the path of the X-ray beam 16. This position of the filters may be preferred for certain imagining operations, such as calibration of the imaging system. In another example position of the first and second filter assemblies 50, 52, the beam hardening filter 64 of the first filter assembly 50 and a bowtie filter of the second filter assembly 52 (e.g., the second bowtie filter 60) may both be positioned within the path of the X-ray beam 16. In this illustrated position, the beam hardening filter 64 overlaps the second bowtie filter 60.

FIGS. 8-10 illustrate cross-sectional views of alternative configurations of a first integrated filter assembly 50 of FIGS. 3-4 and a second integrated filter assembly 52 of FIGS. 5-6 positioned within the example CT imaging system 10 of FIG. 1. In the example configuration illustrated in FIG. 8, the first filter assembly 50 is the same as the example first filter assembly 50 described in FIGS. 3-4. However, the second filter assembly 52 includes a beam hardening filter 96 positioned between the second and third bowtie filters 60, 62. FIG. 9 depicts an alternate configuration in which the first filter assembly 50 does not include a beam hardening filter, and the second filter assembly 52 includes a beam hardening filter 112 coupled to an edge 114 of a top surface 116 of the second carriage 56. The example beam hardening filter 112 may be similar to the beam hardening filter 64 described in conjunction with FIGS. 3-4. In FIG. 10, the depicted alternative configuration includes a first filter assembly 50 that does not include a beam hardening filter, and a second filter assembly 52 that includes a beam hardening filter 112 coupled to the edge 114 of the top surface 116 of the carriage 56 and the beam hardening filter 96 positioned between the second and third bowtie filters 60, 62. While three alternative configurations are depicted in FIG. 8-10, any number of configurations of filter assemblies may be used with a beam hardening filter (e.g., beam hardening filter 64, 96) coupled to an edge of a top surface of a carriage, as described herein.

As illustrated in FIGS. 7A, 7B and 8-10, an additional filter 110, 111 may be coupled to the underside of the carriages 56, 54 and may extend along the entire lower surface of the carriages 56, 54. The filter may further condition the X-ray beam 16 after the beam has passed through one or more of the beam hardening filter and bowtie filters.

During a calibration scan or an imaging scan, an X-ray beam 16 may first pass through the beam hardening filter 64 or 112 followed by a bowtie filter (e.g., a bowtie filter 58, 60, or 62). The carriages 54, 56 may be moved along a direction perpendicular to that of the X-ray beam 16 as illustrated by arrows 53 in FIG. 7A to position the X-ray beam to pass through a bowtie filter 58, 60, 62 and/or a beam hardening filter 64 or 112. A level of beam attenuation and spatial distribution may be adjusted by selecting a beam hardening filter 64 or 112 and/or bowtie filters 58, 60, 62. In one example, the carriages 54, 56 may be positioned such that the X-ray beam passes through the beam hardening filter 64 and the second bowtie filter 60, the beam hardening filter 64 overlapping with the second bowtie filter 60. In another example, the carriages 54, 56 may be positioned such that the X-ray beam passes through the first bowtie filter 58, the second bowtie filter 60, or the third bowtie filter 62. In yet another example, the carriages 54, 56 may be positioned such that the X-ray beam passes through the beam hardening filter 64 or 112. After passing through one of the second or third bowtie filters 60, 62, the X-ray beam also passes through the additional filter 110 before entering a subject. In some examples, the second carriage 56 may be positioned such that the X-ray beam passes through the beam hardening filter 96 on the second carriage 56 and one of the second or third bowtie filters 60, 62. In some examples, the second carriage 56 may be positioned such that the X-ray beam passes through the beam hardening filter 96 on the second carriage 56.

Attenuation of the X-ray beam via a beam hardening filter may be specifically desired during a scout scan which may precede a diagnostic scan. During a diagnostic scan, a bowtie filter without the beam hardening filter may be used for diagnostic scans. Typically, for a scout scan a smaller beam (coverage) may be used relative to the beam size used for diagnostic scans. The smaller beam may pass through the beam hardening filter 96 which is narrower than a bowtie filter. Also, by using a beam hardening filter 64, 96, a higher power X-ray source with increased X-ray tube temperature may be used during a scan without increasing X-ray exposure of or dose to the subject. The higher power may improve the image quality of the scout scan and/or subsequent diagnostic scans and improve thermal stability of the X-ray tube including the target. The higher temperature of the X-ray tube target may contribute to long-term reliability of the device as it remains closer to an optimal operating temperature; fewer temperature cycles of the internal parts contribute to increased reliability.

FIGS. 11A-11F show a variety of example positions of the filter assemblies 50, 52. In particular, FIGS. 11A-11F depict three bowtie filters 58, 60, 62 in their respective carriages 54, 56 and a beam hardening filter 64 in the first filter assembly 50. In this example, a first bowtie filter 58 and the beam hardening filter 64 are positioned together in a first filter assembly 50, and the second and third bowtie filters 60, 62 are positioned within the second filter assembly 52.

A first carriage 54 of the first filter assembly 50 may be coupled to a first shaft 120, and the carriage 54 may be translated along the first shaft 120 by rotating the first shaft 120 with a first motor 122. The first shaft 120 may be a screw, a ball screw, or other similar design to translate rotational motion into linear motion of the first carriage 54. The second carriage 56 of the second filter assembly 52 may be coupled to a second shaft 126 and may be translated along the second shaft 126 by rotating the second shaft 126 with a second motor 128. The second shaft 126 may be a screw, a ball screw, or other similar design to translate rotational motion into linear motion of the second carriage 56. A localized clearance feature (not shown) is present in the second carriage 56 to avert interference of the first shaft 120 with the second carriage 56 as the second carriage 56 translates along the second shaft 126. The position of the X-ray beam passing through the collimator assembly is represented as 103 in FIG. 11A and the center of the X-ray beam is indicated by a horizontal line 16. One of the three bowtie filters 58, 60, 62 along with the beam hardening filter 64 may be selectively translated into the beam path of the X-ray beam 16 by rotating one or both shafts 120, 126 via motors 122, 128, respectively. The first and the second shafts 120, 126 may be aligned in one line, and are spaced apart from each other by a gap. The X-ray beam 16 may transmit through the gap. The motor (such as motor 122, 128), the shaft (such as shaft 120, 126) coupled to the motor 122, 128, and the filter assembly (such as filter assembly 50, 52) coupled to the shaft 120, 126 may form a carriage driving system 130, 132, such as a motor for moving the filters in and out of the X-ray beam. The filter assembly 50, 52 may include one or more carriage driving systems 130, 132.

FIG. 11A shows a first position 134 of the filter assemblies 50, 52. The X-ray beam 16 transmits through a collimator housing 136 as shown by 103 without passing through any filter. The first carriage 54 may be located closer to the first motor 122, and the second carriage 56 may be located closer to the second motor 128.

FIG. 11B shows a second position 138 of the filter assemblies 50, 52. The X-ray beam 16 transmits though the third bowtie filter 62 in the second carriage 56. The second filter assembly 52 may move from the first position 134 to the second position 138 by actuating the second motor 128 and translating the third bowtie filter 62 in carriage 56 into the X-ray beam path 16.

FIG. 11C shows a third position 140 of the filter assemblies 50, 52. The X-ray beam 16 solely transmits though the second bowtie filter 60 in the second carriage 56. The second carriage 56 may move from the first position 134 or the second position 138 to the third position 140 by actuating the second motor 128 and translating the second bowtie filter 60 into the X-ray beam path 16.

FIG. 11D shows a fourth position 142 of the filter assemblies 50, 52. The X-ray beam 16 transmits through the beam hardening filter 64. The filter assembly 50 may move from any of the above-mentioned first 134, second 138, or third position 140 to the fourth position 142 by actuating the first motor 122 to translate the first carriage 54 further from the first motor 122, and subsequently or simultaneously actuating the second motor 128 to translate the second carriage 56 out of the X-ray beam path 16, as needed.

FIG. 11E shows a fifth position 144 of the filter assemblies 50, 52. The X-ray beam 16 transmits through the beam hardening filter 64 and the second bowtie filter 60. The filter assemblies 50, 52 may move from any of the above-mentioned first 134, second 138, third 140, or fourth 142 position to the fifth position 144 by actuating the first motor 122 to translate the first carriage 54 relative to the first motor 122, as needed, and subsequently or simultaneously actuating the second motor 128 to translate the second bowtie filter 60 in the second carriage 56 into the X-ray beam path 16, as needed.

FIG. 11F shows a sixth position 146 of the filter assemblies 50, 52. The X-ray beam 16 transmits through the first bowtie filter 58. The filter assembly 50 may move from any of the above-mentioned first 134, second 138, third 140, fourth 142, and fifth 144 position to the sixth position 146 by actuating the first motor 122 to translate the first carriage 54 further from the first motor 122, and subsequently or simultaneously actuating the second motor 128 to translate the second carriage 56 out of the X-ray beam path 16, as needed.

Based on the instructions stored in the non-transient memory, the computing device (such as computer 36 of FIG. 2) may move the filter assemblies 50, 52 from any one of the above positions to another position by actuating one or more of the two motors 122, 128. In one embodiment, one filter and a beam hardening filter are positioned in one carriage and two filters are positioned in the other carriage. As one example, the two filters may be coupled to one shaft and driven by one motor. In another embodiment, more than three filters and multiple beam hardening filters may be arranged within the collimator housing 136. For example, the numbers of filters coupled to each shaft are the same, if the total number of filters in the housing is even. The numbers of filters coupled to each shaft is different, if the total number of filters in the housing is odd.

In yet another embodiment, the arrangement of the filters in the collimator housing 136 may be based on the type of the filters. Herein, the filter type may be determined by the section of the subject that the filter is designed to image. For example, the first bowtie filter 58 used for imaging the first section of the subject 22 and the second bowtie filter 60 used or imaging the second section of the subject 22 may be positioned next to each other, if the first section and the second section are connected. The first bowtie filter 58 and the second bowtie filter 60 may be positioned apart from each other (such as separated by another filter), if the first section and the second section are not connected. As an example, the filter for imaging the abdomen maybe positioned next to the filter for imaging the chest, but apart from the filter for imaging the head. In this way, when the chest is imaged after imaging the abdomen, the switching of filters is simpler to achieve with less overall carriage motion. The beam hardening filter may be coupled between two filters which may be used for a scout scan. Locating the beam hardening filter in this location makes the switching from scout scan to diagnostic scanning simpler with less overall carriage motion.

In other embodiments, a carriage including filters may be translated with any one of a rack and pinion, a belt, or a cable-driven system in lieu of a shaft.

FIGS. 12A-12C depicts schematic diagrams illustrating components of scans using the example filter assembly in various positions described in relation to FIGS. 11A-11F. For example, FIG. 12A depicts an example schematic diagram of a scan using the CT imaging system 10 where the filter assemblies 50, 52 are arranged such that a bowtie filter is in the path of the X-ray beam 16. For example, FIG. 12A depicts the filter assemblies 50, 52 in one of the second 138, third 140 or sixth 146 positions, where one of the bowtie filters 58, 60, 62 is in the path of the X-ray beam 16. FIG. 12B depicts an example schematic diagram of a scan using the CT imaging system 10 where the filter assemblies 50, 52 are arranged such that a bowtie filter and a beam hardening filter are in the path of the X-ray beam 16. For example, FIG. 12B depicts the filter assemblies 50, 52 in the fifth position 144, where the second bowtie filter 60 and the beam hardening filter 64 are in the path of the X-ray beam 16. FIG. 12C depicts an example schematic diagram of a scan using the CT imaging system 10 where the filter assemblies 50, 52 are arranged such that a beam hardening filter is in the path of the X-ray beam 16. For example, FIG. 12C depicts the filter assemblies 50, 52 in the fourth position 142, where the beam hardening filter 64 is in the path of the X-ray beam 16.

In this way, FIGS. 1-12C provide a CT imaging system, comprising a gantry for receiving an imaging subject, an X-ray source positioned in the gantry for emitting X-rays, an X-ray detector positioned in the gantry opposite to the X-ray source, a motorized table for moving the imaging subject or patient into and out of an opening within the gantry, a computation device with instructions stored in non-transient memory, carriages mounted to the gantry, one or more bowtie filters positioned within one of the filter carriages, and at least one beam hardening filter positioned in one of the filter carriages, and a carriage driving system for switching filters by moving one of the bowtie filters and/or one of the hardening filters into or out of the X-ray beam.

FIGS. 13 and 14 are graphical representations of energy spectrum curves that depict the effect of beam hardening filter 64 of FIG. 3 depending on the material, such as tungsten. Using the tungsten beam hardening filter results in a mono-energy X-ray beam of the specific energy (e.g., 69.5 keV, FIG. 13). The mono-energy X-ray beam is used for the energy calibration of a photon counting X-ray detector. It may also be used for scanning to achieve improved image quality since a mono-energy X-ray beam is an ideal X-ray source for various imaging applications if high X-ray intensity can be achieved. A beam hardening filter absorbs low energy X-rays and passes through high energy X-rays, FIG. 14, that are used for patient imaging. Since it is increasing the average energy of the X-rays, it is called a beam hardening filter. Those low energy X-rays are mostly expected to be absorbed in patients as well and so, not contributing patient image quality but increasing patient dose. FIG. 13 and FIG. 14 show different filter characteristics, but they both are called a beam hardening filter in this document.

FIG. 15 shows an example method 200 for performing calibration scans using beam hardening filter(s) in an integrated filter assembly (such as integrated filter assemblies 50, 52 in described here). Method 200 achieves calibration of an X-ray detector of an imaging system (such as CT imaging system 10) by using a beam hardening filter (such as beam hardening filter 64) that is positioned within a filter assembly. Additionally, a phantom may be used during the calibration, or the calibration may be performed as an air scan. Method 200 and all methods described herein may be performed according to instructions stored in the non-transitory memory in a computing device (such as computer 36 of FIG. 2) of the CT imaging system 10.

At 202, a subject (such as subject 22 in FIG. 2, a phantom, or no subject) of the calibration scans may be positioned on a motorized table (such as table 46 in FIG. 1). A table motor controller 44 may move the table 46 so that a proper section of the subject 22 is within the gantry 12 for imaging.

At 204, the routine includes determining if a calibration scan is desired. A calibration scan may be used to calibrate one or more components of the imaging system, including X-ray detector, X-ray source, X-ray dose, gantry weight balance, and/or software or firmware used to process data collected by the imaging system. Calibration scans may also be used to detect misalignment in the imaging system.

If it is determined that a calibration scan is desired, at 206, scan parameters may be set up for carrying out a calibration scan. For example, a user may input or select the scan parameters according to a scanning protocol or a menu. The scan parameters may include the type and sequence of the filters that are going to be used during the scan. As an example, for a calibration scan a beam hardening filter may be used for conditioning the X-ray beam used for imaging the subject. Scan parameters may also include setting scan timing. As one example, the scan timing may include a start time and a duration for imaging each section.

At 208, a beam hardening filter may be positioned in the path of the X-ray beam by operating a motor coupled to a carriage including the beam hardening filter (such as beam hardening filter 64 in FIG. 3). The carriage may be moved along a shaft in a plane perpendicular to the plane of the X-ray beam to position the beam hardening filter in the X-ray beam. The controller may actuate the motor to move the shaft and the carriage to the desired position. A beam hardening filter may intercept lower energy X-rays, thereby attenuating and "hardening" the X-ray beam.

At 210, method 200 may start acquiring the dataset of the calibration scan. For example, the X-ray source (such as 14 of FIG. 2) may be activated, and X-ray exposure of the subject through the beam hardening filter may be started.

The dataset is acquired from the X-ray detector (such as 15 of FIG. 2) upon receiving attenuated X-rays from the subject being imaged. As one example, the anatomy or positioning of the subject may be monitored by analyzing the acquired dataset. The currently imaged location may be calculated based on the starting location of the scan and the travel distance of the motorized table. In one embodiment, the anatomies or positions of the subject may be grouped in different types. As another example, the collected data can be analyzed, for example, K-edge search to locate 69.5 keV in electronics and produce its result. The result can be used to decide to finish or repeat the calibration.

At 212, the routine includes determining if the calibration scan has ended. The end of the calibration scan may be determined based on the protocol setup at step 206. If it is determined that the calibration scan has not ended, at 214, the scout scan may be continued, and data may be acquired. If it is determined that the calibration scan has ended, the calibration is complete.

FIG. 16 shows an example method 300 for performing image scans using multiple filters included in an integrated filter assembly (such as integrated filter assembly 50, 52). Method 300 achieves image acquisition of the imaging subject by changing filters between successive scans. Method 300 and all methods described herein may be performed according to instructions stored in the non-transitory memory in a computing device (such as computer 36 of FIG. 2) of the CT imaging system.

At 302, a subject (such as subject 22 in FIG. 2) of the imaging scans may be positioned on a motorized table (such as table 46 in FIG. 2). A table motor controller 44 may move the table so that a proper section of the subject is within the gantry for imaging.

At 304, the routine includes determining if a scout scan is desired. A scout scan provides a projection view along a longitudinal axis of the imaging subject and generally provides aggregations each including internal structures of the subject. During a scout scan, while all the components of the imaging system may be maintained in a stationary position, the subject may be passed through the imaging system to perform a scan on the subject. A scout scan may be used to identify a region of interest of the subject for a subsequent diagnostic scan.

If it is determined that a scout scan is desired, at 306, scan parameters may be set up for carrying out a scout scan. For example, a user may input or select the scan parameters according to a scanning protocol or a menu. The scan parameters may include the type and sequence of the filters that are going to be used during the scan. As an example, for a scout scan a bowtie filter along with a beam hardening filter may be used for conditioning the X-ray beam used for imaging the subject. Scan parameters may also include setting scan timing. As one example, the scan timing may include a start time and a duration for imaging each section.

At 308, a bowtie filter and a beam hardening filter may be positioned in the path of the X-ray beam by operating a motor(s) coupled to a carriage(s) including the bowtie filter (such as bowtie filter 60 in FIG. 6) and the beam hardening filter (such as beam hardening filter 64 in FIG. 3). The carriage(s) may be moved along a shaft in a plane perpendicular to the plane of the X-ray beam to position the bowtie filter and the beam hardening filter in the X-ray beam. The controller may actuate the motor to move the shaft and the carriage to the desired position. The bowtie filter may change the spatial distribution of the X-ray beam in the axial plane of the subject (such as a patient). For example, the re-distributed X-ray beam may have higher energy at the center and lower energy at the periphery of the subject. A beam hardening filter may intercept lower energy X-rays, thereby attenuating and "hardening" the beam. The beam hardening filter may at least partially overlap with the bowtie filter and the beam may first pass through the beam hardening filter and then enter the bowtie filter.

At 310, method 300 may start acquiring the dataset of the subject. For example, the X-ray source (such as 14 of FIG. 2) may be activated, and X-ray exposure of the subject through the bowtie filter and the beam hardening filter may be started. For a scout scan, a smallest permissible beam may be used. In one example, the beam may be 5 mm. By using a beam hardening filter to attenuate the beam reaching the subject, a higher power X-ray source with increased X-ray tube temperature may be used during the scout scan without increasing X-ray exposure of the subject. The higher power improves the quality of the diagnostic scan and improves thermal stability of the X-ray tube including the target. In one example, a 50 kW X-ray power scan technique (100 kV, 500 mA) may be used.

The dataset is acquired from the X-ray detector (such as 15 of FIG. 2) upon receiving the transmitted radiation signal from the subject. As one example, the anatomy of the subject may be monitored by analyzing the acquired dataset. As another example, the anatomy of the subject may be estimated by the currently imaged location. The currently imaged location may be calculated based on the starting location of the scan and the travel distance of the motorized table. In one embodiment, the anatomies of the subject may be grouped in different types. For example, the anatomy of a human body may be grouped based on size, type such as the head, the chest, and the abdomen.

At 312, the routine includes determining if the scout scan has ended. The end of the scout scan may be determined based on the protocol setup at step 306. If it is determined that the scout scan has not ended, at 314, the scout scan may be continued, and data may be acquired.

If it is determined that the scout scan has ended, at 316, the routine includes determining if a diagnostic scan is desired. As an example, a decision to carry out the diagnostic scan may be made based on the images reconstructed from the data acquired during the scout scan. The image from the scout scan may be two-dimensional or three-dimensional. Based on the scout scan, a specific anatomy may be selected for a diagnostic scan. The diagnostic scan may provide a detailed image of the specific anatomy which might not be available via the scout scan.

If at 304, it is determined that a scout scan is not desired, the routine may directly proceed to step 316 for determining if a diagnostic scan is desired. A scout scan may not precede a diagnostic scan.

If it is determined that a diagnostic scan is not desired and a scout scan has been completed, at 318, the acquired dataset from the scout scan is displayed and stored. In one embodiment, dataset acquired from different sections of the subject may be re-constructed to form an image. The acquired dataset, as well as the processed images may be saved in the storage of the imaging system and no further scans may be carried out. The routine may then end.

If it is determined that a diagnostic scan is desired, the routine may proceed to step 320 wherein the scan parameters may be set up for carrying out a diagnostic scan. A user may input or select the scan parameters according to a scanning protocol or a menu. The scan parameters may include the type and sequence of the filters that are going to be used during the scan. The type of the filters may be chosen based on the anatomy of imaging subject that is to be imaged. The parameters may also include setting scan timing. As one example, the scan timing may include a start time and a duration for imaging each section. Anatomy information of the imaging subject may be loaded to the memory of the computation device. The anatomy information may be acquired from a pre-scan. The anatomy information may be acquired from the prior scout scan or a localized scan. This step may also include moving the imaging subject via the motorized table so that the proper section of the subject is within the gantry for imaging.

At 322, a contrast agent may be injected into the imaging subject. The contrast agent may enhance the contrast of images captured specifically for certain anatomies. This step is optional, and the diagnostic scan may be carried out without use of a contrast agent.

At 324, a bowtie filter may be positioned in the path of the X-ray beam by operating a motor coupled to a carriage including the bowtie filter. The type of the filter may be determined based on the anatomy of the currently imaged section of the subject. The carriages may be moved along a shaft in a plane perpendicular to the plane of the X-ray beam to position the bowtie filter in the beam. In one example, the bowtie filter used for the diagnostic scan may be same as the bowtie filter used in the scout scan. In another example, the bowtie filter used for the diagnostic scan may be different from the bowtie filter used in the scout scan. In this way, a single carriage including one or more bowtie filters and/or a beam hardening filter may be used for both the scout scan and the diagnostic scan without the need for additional components. Furthermore, multiple filter carriages can be used together to position a bowtie filter with or without a beam hardening filter into the X-ray beam.

At 326, dataset of the subject may be acquired. For example, the X-ray source may be activated, and X-ray exposure of the subject through the selected bowtie filter may be started. For a diagnostic scan, a beam size of approximately 25 mm to 160 mm at the filter assembly may be used. The dataset is acquired from the X-ray detector upon receiving the transmitted radiation signal from the imaging subject. As one example, the anatomy of the imaging subject may be monitored by analyzing the acquired dataset. As another example, the anatomy of the imaging subject may be estimated by the currently imaged location. The currently imaged location may be calculated based on the starting location of the scan and the travel distance of the motorized table. In one embodiment, the anatomies of the subject may be grouped in different types. For example, the anatomy of a human body may be grouped based on size, types of such as the head, the chest, and the abdomen.

At 328, the routine includes determining if the diagnostic scan has ended. The end of the diagnostic scan may be determined based on the protocol setup at step 320. If it is determined that the diagnostic scan has not ended, a 330, the diagnostic scan may be continued, and data may be acquired.

If it is determined that the diagnostic scan has ended, the acquired dataset from the diagnostic scan is displayed and stored. In one embodiment, dataset acquired from different sections of the subject may be re-constructed to form an image. The acquired dataset, as well as the processed images may be saved in the storage of the imaging system and no further scans may be carried out. The routine may then end.

In this way, during a first imaging (such as a scout scan), carriages may be moved to position a beam hardening filter and a first bowtie filter housed in the carriages in a path of an X-ray beam between an X-ray source and an imaging subject and during a second imaging (such as a diagnostic scan), the carriages may be moved to move the beam hardening filter and the first bowtie filter out of the path of the X-rays and then position a second bowtie filter housed in the carriage in the path of the X-rays.

The technical effect of attenuating a beam reaching the subject by using a beam hardening filter is that a higher-powered X-ray source with increased X-ray tube temperature may be used during a scan without increasing X-ray exposure of the subject. Overall, the higher power improves the quality of the diagnostic scan and improves thermal stability of the X-ray tube including the target.

In one example, an imaging system, includes a carriage with one or more beam hardening filters and one or more bowtie filters. A carriage driving system moves carriage to selectively position the one or more beam hardening filters and the one of the one or more bowtie filters in a path of an X-ray beam between an X-ray source and a subject. The one or more beam hardening filters extends from an edge of the carriage and may overlap with a bowtie filter in a second carriage. The one or more beam hardening filters extending from the carriage may be coupled to the carriage using a support structure. In the preceding example method, additionally or optionally, one or more beam hardening filter may partially overlap with the one or more bowtie filters. In any or all of the preceding examples, additionally or optionally, the one or more bowtie filters include a first bowtie filter and a second bowtie placed adjacent to each other within the carriage. In any or all of the preceding examples, additionally or optionally, a beam hardening filter is placed between the first bowtie filter and the second bowtie filter, the beam hardening filter partially overlapping with each of the first bowtie filter and the second bowtie filter. In any or all of the preceding examples, additionally or optionally, the first bowtie filter is housed within a first slot formed in a cavity of the carriage and wherein the second bowtie filter is housed within a second slot formed in the cavity of the carriage, the first slot separated from the second slot via a tab. In any or all of the preceding examples, additionally or optionally, the beam hardening filter is embedded within a recess between the first bowtie filter and the second bowtie filter, the one or more beam hardening filters coupled to the tab. In any or all of the preceding examples, additionally or optionally, each of the beam hardening filter includes a support structure and one or more metal sheets, the support structure and the one or more metal sheets stacked together and coupled to the tab via a plurality of fasteners. In any or all of the preceding examples, additionally or optionally, the support structure and the one or more metal sheets may be of a same dimension, and the support structure may be made of a material different from that of the one or more metal sheets.

In any or all of the preceding examples, additionally or optionally, the X-ray beam passed through the one or more beam hardening filters, then one of the one or more bowtie filters, and the aluminum filter prior to entering the subject. In any or all of the preceding examples, additionally or optionally, the carriage driving system includes a motor coupled to the carriage via a shaft, the motor operated to translate the shaft for positioning the one or more beam hardening filters and the one of the one or more bowtie filters in the path.

Another example method for an imaging system includes, during a first imaging, moving a carriage to position a beam hardening filter and a first bowtie filter housed in the carriage in a path of a X-ray beam between a X-ray source and an imaging subject, and during a second imaging, moving the carriage to move the beam hardening filter and the first bowtie filter out of the path of the X-ray and then position a first bowtie filter or a second bowtie filter housed in the carriage in the path of the X-ray. In the preceding example method, additionally or optionally, the first imaging is a scout scan, and a second imaging is a diagnostic scan of an anatomy of the imaging subject, a beam size used in the first imaging smaller than a beam size used in the second imaging. In any or all of the preceding examples, additionally or optionally, the moving the carriage includes actuating a motor coupled to the carriage via a shaft, the shaft translating in a direction perpendicular to a direction of the path of the X-ray to position one or more of the beam hardening filters, the first bowtie filter, and the second bowtie filter in the path of the X-ray. In any or all of the preceding examples, additionally or optionally, each of the first bowtie filter and the second bowtie filter are positioned inside corresponding, adjacent slots within the carriage and the beam hardening filter is coupled to the carriage between the first bowtie filter and the second bowtie filter. In any or all of the preceding examples, additionally or optionally, the beam hardening filter partially overlaps with each of the first bowtie filter and the second bowtie filter, and herein, during the first imaging, the X-ray beam first passes through the beam hardening filter and then passes through the first bowtie filter. In any or all of the preceding examples, additionally or optionally, one or more beam hardening filters extends from a first carriage and may be moved to overlap a bowtie filter positioned within a second carriage.

In yet another example, a system for an imaging system, includes a gantry for receiving an imaging subject, a X-ray source positioned in the gantry for emitting X-ray exposure, an X-ray detector positioned on the opposite of the gantry relative to the X-ray source, a motorized table for moving the imaging subject within the gantry, a computation device with instructions stored in a non-transient memory, a one or more bowtie filters, and one or more beam hardening filters positioned in the filter carriage. The one or more beam hardening filters may extend from the carriage. In some examples, the one or more beam hardening filter may overlap with a bowtie filter of a second carriage. Additionally or alternatively, the one or more beam hardening filters may be mounted in between a first bowtie filter of the one or more bowtie filters and a second bowtie filter of the one or more filters, partially overlapping with each of the first bowtie filter and the second bowtie filter. A carriage driving system for switching filters by moving one or more of the bowtie filters, and/or the one or more beam hardening filters into or out of the X-ray beam. In the preceding example system, additionally or optionally, each of the bowtie filters includes a first, straight long side and a second, parallel long side including a central ridge. Each of the bowtie filters is made of graphite. In any or all of the preceding examples, additionally or optionally, the beam hardening filter includes each of a support structure, and one or more metal sheets stacked under the support structure. In any or all of the preceding examples, additionally or optionally, the rectangular support structure is made of aluminum and the one or more metal sheets are made of copper with each of the one or more metal sheets having a different thickness.

FIGS. 3-12C show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with a space in-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the subject matter of the disclosure, including the best mode, and also to enable a person of ordinary skill in the relevant art to practice the subject matter of the disclosure, including making and using any devices or systems and performing any incorporated methods. The patentable scope of the subject matter of the disclosure is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging system, comprising:
a collimator assembly, the collimator assembly positioned adjacent to an X-ray source, the X-ray source generating an x-ray beam through the collimator assembly, wherein the collimator assembly includes:
at least one carriage including at least one beam hardening filter and at least one bowtie filter, wherein the beam hardening filter is coupled to an edge of the carriage and extends away from the at least one bowtie filter, wherein the beam hardening filter includes one or more metal sheets and a support structure having a window frame member and a bottom support member, wherein the one or more metal sheets are positioned between the window frame member and the bottom support member.

2. The imaging system of claim 1, further including a carriage driving system for moving the at least one carriage to selectively position one of the at least one beam hardening filter and the at least one bowtie filter in and out of a path of the X-ray beam.

3. The imaging system of claim 2, wherein the carriage driving system includes a motor coupled to the carriage via a shaft, the motor operated to translate the shaft for positioning one of the at least one beam hardening filter and the at least one bowtie filter in and out of the path of the X-ray beam.

4. The imaging system of claim 1, wherein the at least one carriage is a first carriage, and further comprising a second carriage, wherein the second carriage includes one or more bowtie filters, and wherein the at least one beam hardening filter of the first carriage may be moved into a position to overlap with one of the one or more bowtie filters of the second carriage.

5. The imaging system of claim 1, wherein the at least one beam hardening filter is a heavy element material that emits mono-energy X-rays for energy calibration of an X-ray detector.

6. The imaging system of claim 4, wherein the at least one bowtie filter of the first carriage is a first bowtie filter, and wherein the one or more bowtie filters of the second carriage includes a second bowtie filter and a third bowtie filter positioned adjacent to each other within the second carriage.

7. The imaging system of claim 6, wherein the first bowtie filter is positioned within a first slot formed in the first carriage and wherein the second bowtie filter is positioned within a second slot formed in the second carriage and the third bowtie filter is positioned within a third slot formed in the second carriage, the first slot separated from the second slot via a tab.

8. The imaging system of claim 4, wherein the at least one beam hardening filter is coupled to a top surface of the edge of the first carriage such that the beam hardening filter may be moved into a position above one of the one or more bowtie filters of the second carriage to overlap with one of the one or more bowtie filters of the second carriage.

9. The imaging system of claim 4, wherein the at least one beam hardening filter of the first carriage may be moved into a position where the X-ray beam passes through the at least one beam hardening filter.

10. The imaging system of claim 1, wherein the at least one beam hardening filter includes a support structure and one or more metal sheets, the support structure and the one or more metal sheets are stacked together and coupled to the at least one beam hardening filter via a plurality of fasteners.

11. The imaging system of claim 10, wherein the support structure and the one or more metal sheets are a same dimension, and wherein the support structure is made of a material different from that of the one or more metal sheets.

12. A method for an imaging system, comprising:
during a first imaging, moving a first carriage to position a beam hardening filter coupled to an edge of the first carriage in a path of an X-ray beam and moving a second carriage to position a second bowtie filter housed in the second carriage in the path of the X-ray beam; and during a second imaging, moving the first carriage to move the beam hardening filter out of the path of the X-ray beam, wherein the beam hardening filter includes one or more metal sheets and a support structure having a window frame member and a bottom support member, wherein the one or more metal sheets are positioned between the window frame member and the bottom support member.

13. The method of claim 12, further comprising, during the second imaging, moving the first carriage or the second carriage to position a first bowtie filter, the second bowtie filter, or a third bowtie filter in the path of the X-ray beam.

14. The method of claim 12, wherein the first imaging is a scout scan, and the second imaging is a diagnostic scan, and wherein an X-ray beam size used in the first imaging is smaller than an X-ray beam size used in the second imaging.

15. The method of claim 12, wherein the moving the first carriage includes actuating a motor coupled to the first carriage via a shaft, the shaft translating the first carriage in a direction perpendicular to a direction of the path of the X-ray beam to position the beam hardening filter into or out of the path of the X-ray beam.

16. The method of claim 12, wherein each of the second bowtie filter and the third bowtie filter are positioned inside corresponding, adjacent slots within the second carriage and the beam hardening filter is coupled to the first carriage adjacent to the first bowtie filter, wherein the beam hardening filter is attached to a top surface of the first carriage such that the beam hardening filter may extend over the second bowtie filter.

17. The method of claim 12, wherein the beam hardening filter overlaps with the second bowtie filter and wherein, during the first imaging, the X-ray beam first passes through the beam hardening filter and then passes through the second bowtie filter.

18. A computed tomography (CT) imaging system, comprising:
   a gantry;
   an X-ray source positioned in the gantry for emitting X-rays;
   an X-ray detector positioned in the gantry opposite the X-ray source;
   a first carriage including a first bowtie filter and a first beam hardening filter, wherein the first beam hardening filter is coupled to an edge of the first carriage and wherein the first beam hardening filter includes one or more metal sheets and a support structure having a window frame member and a bottom support member, wherein the one or more metal sheets are positioned between the window frame member and the bottom support member;
   a second carriage including a second bowtie filter and a third bowtie filter with a second beam hardening filter positioned between the second bowtie filter and the third bowtie filter; and
   a carriage driving system for switching filters by moving one or more of the first bowtie filter, the second bowtie filter, the third bowtie filter, and the first beam hardening filter, the second beam hardening filter into or out of an X-ray beam.

19. The CT imaging system of claim 18, wherein each of the first bowtie filter and the second bowtie filter include a first, straight long side and a second, parallel long side including a central ridge.

20. The CT imaging system of claim 18, wherein the second beam hardening filter includes a support structure, and one or more metal strips stacked under the support structure.

21. A pre-patient collimator assembly for a computed tomography (CT) imaging system, the pre-patient collimator assembly comprising:
   a first carriage including a beam hardening filter and a first bowtie filter;
   a first carriage driving system coupled to the first carriage for moving the first carriage and thus the beam hardening filter and the first bowtie filter in and out of an X-ray beam path;
   a second carriage including a second bowtie filter and a third bowtie filter; and
   a second carriage driving system coupled to the second carriage for moving the second carriage and thus the second bowtie filter and the third bowtie filter in and out of the X-ray beam path;
   wherein the beam hardening filter is positioned along and coupled to an outer edge of the first carriage using a support structure, wherein the support structure includes a window frame member and a bottom support member; and
   wherein the beam hardening filter may be positioned in the X-ray beam path alone or in combination with one of the second bowtie filter or the third bowtie filter.

* * * * *